US010111641B2

(12) United States Patent
Kwak

(10) Patent No.: US 10,111,641 B2
(45) Date of Patent: Oct. 30, 2018

(54) RADIOGRAPHIC IMAGING APPARATUS AND METHOD OF CONTROLLING THE SAME

(71) Applicant: SAMSUNG ELECTRONICS CO., LTD., Suwon-si (KR)

(72) Inventor: Ho-Seong Kwak, Seoul (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 39 days.

(21) Appl. No.: 14/703,381

(22) Filed: May 4, 2015

(65) Prior Publication Data
US 2015/0313561 A1 Nov. 5, 2015

(30) Foreign Application Priority Data

May 2, 2014 (KR) .................. 10-2014-0053236
Apr. 22, 2015 (KR) .................. 10-2015-0056287

(51) Int. Cl.
*H05G 1/02* (2006.01)
*A61B 6/00* (2006.01)
*A61B 6/10* (2006.01)
*A61B 6/04* (2006.01)

(52) U.S. Cl.
CPC .............. *A61B 6/547* (2013.01); *A61B 6/102* (2013.01); *A61B 6/4482* (2013.01); *A61B 6/0407* (2013.01); *A61B 6/4452* (2013.01); *A61B 6/4464* (2013.01)

(58) Field of Classification Search
CPC ........... A61B 6/547; A61B 6/548; A61B 6/54; A61B 6/00

USPC .................... 378/193, 198, 197, 131, 39, 55
See application file for complete search history.

(56) References Cited

U.S. PATENT DOCUMENTS

| | | | | |
|---|---|---|---|---|
| 5,475,291 | A * | 12/1995 | Yoshida | G05B 13/024 318/560 |
| 6,158,200 | A * | 12/2000 | Taylor | B65B 1/22 53/451 |
| 2004/0234039 | A1* | 11/2004 | Karaus | A61B 6/102 378/196 |
| 2010/0243924 | A1 | 9/2010 | Uchida et al. | |
| 2012/0087479 | A1* | 4/2012 | Moon | A61B 6/4452 378/189 |
| 2012/0155616 | A1 | 6/2012 | Rijken et al. | |
| 2012/0236999 | A1 | 9/2012 | Altvater et al. | |

(Continued)

FOREIGN PATENT DOCUMENTS

JP 2008-246069 A 10/2008
WO 2006/085156 A2 8/2006

OTHER PUBLICATIONS

Communication dated Jul. 29, 2015 issued in International Application No. PCT/KR2015/004121 (PCT/ISA/210).

(Continued)

*Primary Examiner* — Jason McCormack
(74) *Attorney, Agent, or Firm* — Sughrue Mion, PLLC

(57) ABSTRACT

There are provided a radiographic imaging apparatus that is movable in response to a relatively small application of force and a method for controlling the same. A radiographic imaging apparatus includes a radiographic image generator; a motor configured to move the radiographic image generator; and a controller configured to calculate a disturbance applied to the radiographic image generator and to drive the motor based on the disturbance.

23 Claims, 19 Drawing Sheets

(56) References Cited

U.S. PATENT DOCUMENTS

| | | | | |
|---|---|---|---|---|
| 2013/0028388 A1* | 1/2013 | Yoshida | ............... | A61B 6/4441 378/190 |
| 2013/0121477 A1* | 5/2013 | Lee | .......................... | H05G 1/02 378/198 |
| 2014/0119516 A1 | 5/2014 | Yang et al. | | |

OTHER PUBLICATIONS

Communication dated Feb. 20, 2018, issued by the European Patent Office in counterpart European Patent Application 15785393.8.

\* cited by examiner

RADIOGRAPHIC IMAGING APPARATUS AND METHOD OF CONTROLLING THE SAME

CROSS-REFERENCE TO RELATED APPLICATION

This application claims priority from Korean Patent Application No. 10-2014-0053236, filed on May 2, 2014 in the Korean Intellectual Property Office, and from Korean Patent Application No. 10-2015-0056287, filed on Apr. 22, 2015 in the Korean Intellectual Property Office, the disclosures of which are incorporated herein by reference in their respective entireties.

BACKGROUND

1. Field

Exemplary embodiments relate to a radiographic imaging apparatus.

2. Description of the Related Art

A radiographic imaging apparatus is an apparatus configured to obtain an internal image of a human body using X-rays. Radiographic imaging apparatuses are used to examine injuries or diseases inside the human body that may not be identifiable from the outside.

A radiographic imaging apparatus may obtain an internal image of the human body using a method in which X-rays are radiated onto an imaging area such as the head and the chest of the human body and penetrating X-rays are detected.

A radiographic imaging apparatus includes an X-ray tube configured to radiate X-rays onto an imaging area. The X-ray tube is provided to be movable such that various areas of the human body can be examined.

In general, a ceiling-mounted radiographic imaging apparatus includes at least one guide rail that is installed at a ceiling of a laboratory and a post frame that is foldably connected to the guide rail. In addition, the X-ray tube is rotatably installed at a lower end of the post frame.

Due to a weight of the X-ray tube, a frictional resistance in each drive shaft of the radiographic imaging apparatus, and the like, when a user wants to manually move the X-ray tube, the user may be required to apply a large amount of force or torque to the X-ray tube. Therefore, when the X-ray tube is repeatedly moved, the user may feel physical fatigue.

SUMMARY

The disclosed exemplary embodiments provide a radiographic imaging apparatus that is movable in response to a relatively small application of force and a method for controlling the same.

According to an aspect of one or more exemplary embodiments, there is provided a radiographic imaging apparatus, including: a radiographic image generator; a motor configured to move the radiographic image generator; and a controller configured to calculate a disturbance applied to the radiographic image generator and to drive the motor based on the calculated disturbance.

The controller may be further configured to calculate the disturbance by using a feedback signal output from the motor and a control signal which is used for driving the motor.

The controller may be further configured to calculate the disturbance by subtracting a control signal which is used for driving the motor from a feedback signal output from the motor.

The controller may be further configured to determine an amount and a direction of an external force applied to the radiographic image generator from the disturbance.

The controller may be further configured to drive the motor based on an amount and a direction of the external force.

The motor may be further configured to move the radiographic image generator in a direction which corresponds to the direction of the external force by using a driving force which corresponds to the amount of the external force.

The controller may be further configured to control at least one from among a position, a speed, a current, an acceleration, and an angular velocity of the motor based on the amount and the direction of the external force.

The controller may be further configured to generate an input signal for controlling at least one from among a position, a speed, a current, an acceleration, and an angular velocity of the motor based on the external force.

The controller may be further configured to receive an error signal calculated from the generated input signal and a feedback signal output from the motor, to generate a control signal for controlling at least one from among a position, a speed, a current, an acceleration, and an angular velocity of the motor by using at least one from among a proportional control, an integral control, and a differential control, and to transmit the generated control signal to the motor.

The controller may be further configured to remove a signal of a resonance frequency band of the radiographic imaging apparatus from the generated input signal and to transmit a result of the removal to the motor.

A gain of the at least one of the proportional control, the integral control, and the differential control may be preset to have a value which is smaller than a predetermined threshold value.

When the radiographic imaging apparatus operates in a power-assisted mode, the motor is further configured to cause a movement of the radiographic image generator based on a detected amount of a force or torque which is directly applied by a user, and the disturbance is applied based on a motion which results from the caused movement.

According to another aspect of one or more exemplary embodiments, there is provided a method for controlling a radiographic imaging apparatus, including: calculating a disturbance applied to a radiographic image generator; determining an amount and a direction of an external force applied to the radiographic image generator from the disturbance; and moving the radiographic image generator based on the external force.

The calculating the disturbance may include calculating the disturbance by using a feedback signal output from a motor which is configured to move the radiographic image generator and a control signal which is used for driving the motor.

The calculating the disturbance may include calculating the disturbance by subtracting a control signal which is used for driving the motor from a feedback signal output from a motor which is configured to move the radiographic image generator.

The moving the radiographic image generator may include controlling at least one from among a position, a speed, a current, an acceleration, and an angular velocity of a motor which is configured to move the radiographic image generator based on an amount and a direction of the external force.

The moving the radiographic image generator may include: generating an input signal for controlling at least one from among a position, a speed, a current, an acceleration, and an angular velocity of a motor which is configured to move the radiographic image generator based on a level and a direction of the external force; calculating an error signal by subtracting a feedback signal output from the motor from the generated input signal; and controlling at least one from among a position, a speed, a current, an acceleration, and an angular velocity of the motor based on the error signal by using at least one from among a proportional control, an integral control, and a differential control.

The method may further include removing a signal of a resonance frequency band of the radiographic imaging apparatus from the generated input signal.

A gain of the at least one from among the proportional control, the integral control and the differential control may be preset to have a value which is smaller than a predetermined threshold value.

When the radiographic imaging apparatus operates in a power-assisted mode, the calculating the disturbance further comprises calculating the disturbance which is applied based on a motion which results from a force or torque directly applied by a user.

According to an aspect of one or more exemplary embodiments, there is provided a radiographic imaging apparatus, including: a radiographic image generator; a motor configured to move the radiographic image generator; and a controller configured to provide a power-assisted mode and an automatic movement mode, and in the power-assisted mode, to calculate a disturbance applied to the radiographic image generator and drive the motor based on the calculated disturbance, and in the automatic movement mode, to move the radiographic image generator to a movement position of the radiographic image generator if the movement position of the radiographic image generator is input by a user.

The radiographic imaging apparatus may further include a mode switching unit configured to switch the power-assisted mode and the automatic movement mode between each other in response to an input provided by a user.

According to one or more exemplary embodiments, when force or torque is applied to a radiographic image generator in any direction, the motor is operated to correspond thereto. Accordingly, it is possible to minimize an amount of force or torque to be applied by the user to move the radiographic image generator, and the user may easily linearly move or rotate the radiographic image generator to a desired position.

Further, according to one or more exemplary embodiments, when an amount of force to be applied to the radiographic image generator is calculated without using a force/torque sensor, it is possible to reduce a cost necessary for building a configuration for measuring external force using the force/torque sensor.

Still further, according to one or more exemplary embodiments, since a configuration of a separate clutch and brake necessary for moving and stopping the image generator may be omitted, it is possible to reduce a cost and further simplify a structure of the device.

BRIEF DESCRIPTION OF THE DRAWINGS

These and/or other aspects will become apparent and more readily appreciated from the following description of exemplary embodiments, taken in conjunction with the accompanying drawings of which.

DETAILED DESCRIPTION

Hereinafter, exemplary embodiments will be described in detail with reference to the accompanying drawings.

Figure 1:
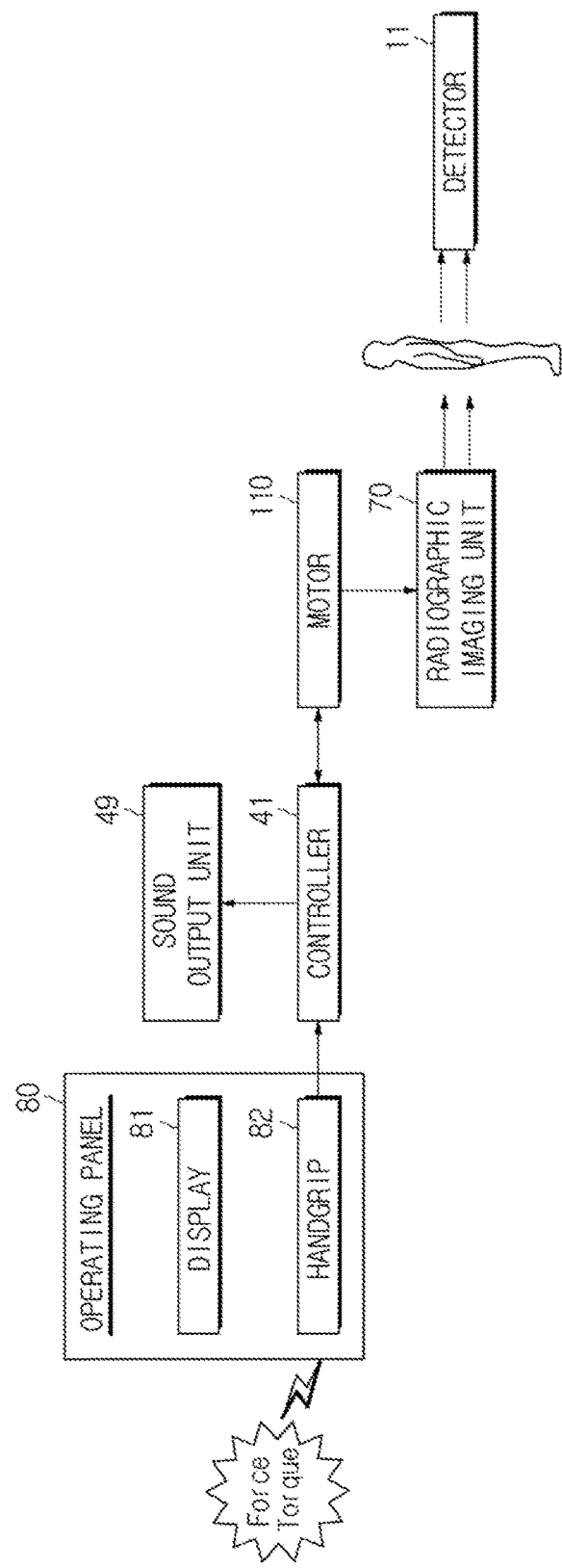
FIG. 1 is a block diagram illustrating a configuration of a radiographic imaging apparatus, according to an exemplary embodiment.
Figure 2:
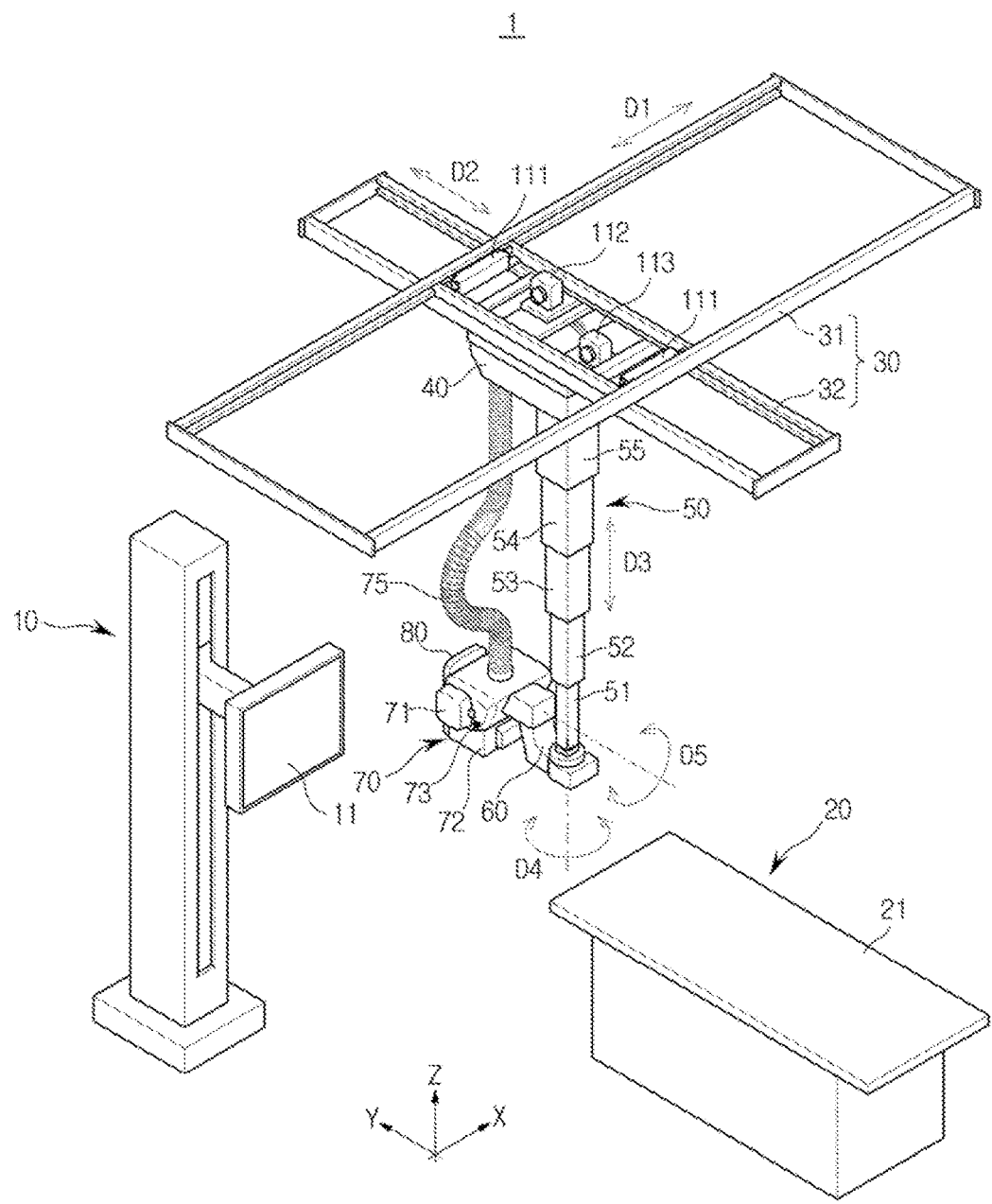
FIG. 2 is a perspective view illustrating a configuration of a radiographic imaging apparatus, according to an exemplary embodiment.
Figure 3:
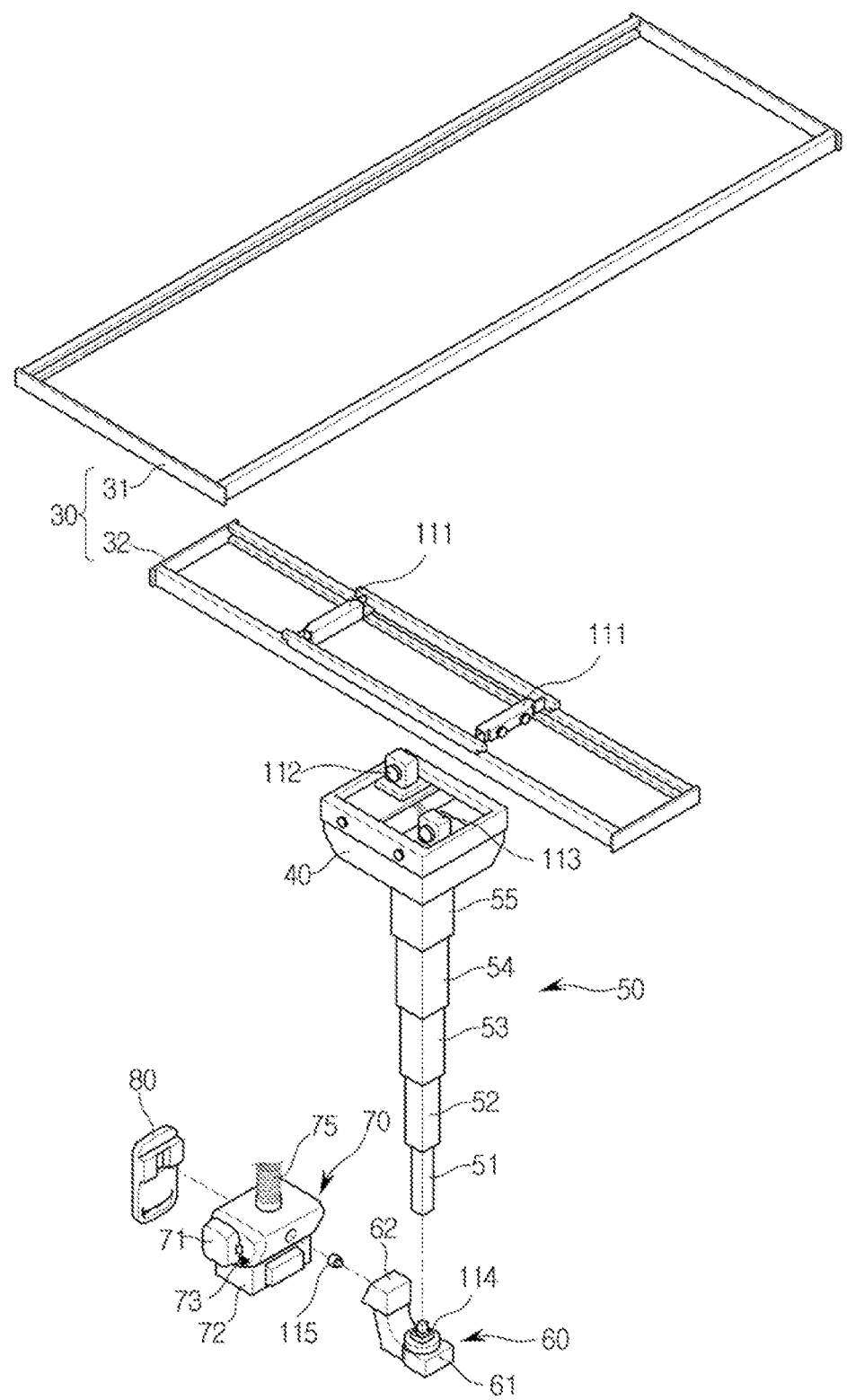
FIG. 3 is an exploded perspective view illustrating a radiographic imaging apparatus, according to an exemplary embodiment.
Figure 4:
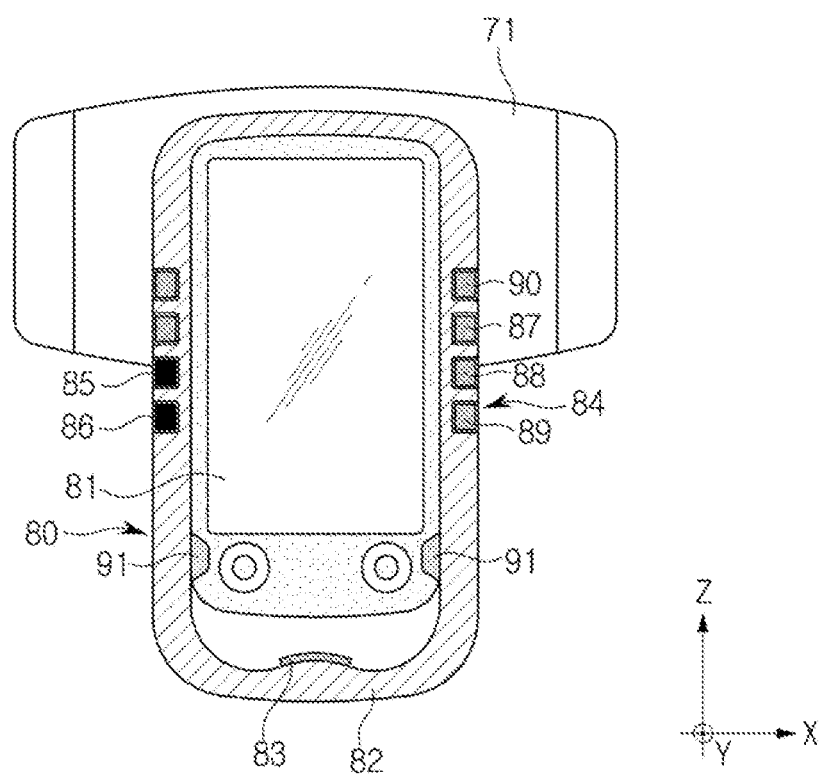
FIG. 4 is a front view illustrating an operating panel of a radiographic imaging apparatus, according to an exemplary embodiment.

FIG. 1 is a block diagram illustrating a configuration of a radiographic imaging apparatus, according to an exemplary embodiment. FIG. 2 is a perspective view illustrating a configuration of a radiographic imaging apparatus, according to an exemplary embodiment. FIG. 3 is an exploded perspective view illustrating a radiographic imaging apparatus, according to an exemplary embodiment. FIG. 4 is a front view illustrating an operating panel of a radiographic imaging apparatus, according to an exemplary embodiment.

As illustrated in FIG. 1, the radiographic imaging apparatus according to the disclosed exemplary embodiment includes an operating panel 80 that provides an interface for operating the radiographic imaging apparatus and includes a handgrip 82 that may be gripped by a user, a controller 41 configured to calculate force or torque that is applied via the handgrip 82 of the operating panel 80 and to generate a control signal for moving a radiographic imaging unit (also referred to herein as a "radiographic image generator") 70 based on the calculation result, a motor 110 configured to provide driving force for moving the radiographic imaging unit 70 according to the control signal of the controller 41, the radiographic imaging unit 70 configured to radiate radiation onto an object and to generate an image of the object, and a detector 11 configured to detect radiation that penetrates through the object.

The above-described components of the radiographic imaging apparatus will be described in further detail with reference to FIGS. 2, 3, and 4.

The radiographic imaging apparatus includes a guide rail 30, a moving carriage 40, the controller 41 provided inside the moving carriage 40, a post frame 50, the motor 110, the radiographic imaging unit 70 and the operating panel 80.

In addition, the radiographic imaging apparatus may further include an imaging stand 10 and an imaging table 20 that include a detecting unit configured to detect X-rays that penetrate through the object.

The guide rail 30, the moving carriage 40, the post frame 50 and the like are provided to move the radiographic imaging unit 70 toward the object.

The guide rail 30 includes a first guide rail (also referred to herein as a "first guide rail member") 31 and a second guide rail (also referred to herein as a "second guide rail member") 32 that are installed so as to form a predetermined angle. The first guide rail 31 and the second guide rail 32 may extend in orthogonal directions.

The first guide rail 31 is installed at a ceiling of a laboratory in which the radiographic imaging apparatus is provided.

The second guide rail 32 is positioned below the first guide rail 31 and is slidably mounted on the first guide rail 31. A roller (not illustrated) that is movable along the first guide rail 31 may be installed in the first guide rail 31. The second guide rail 32 is connected to this roller (not illustrated) and is movable along the first guide rail 31.

A first direction D1 is defined as a direction in which the first guide rail 31 extends. A second direction D2 is defined as a direction in which the second guide rail 32 extends. Therefore, the first direction D1 and the second direction D2 may be arranged to be orthogonal to each other and mutually parallel to the ceiling of the laboratory.

The moving carriage 40 is arranged below the second guide rail 32 so as to move along the second guide rail 32. A roller (not illustrated) may be installed in the moving carriage 40 so as to move along the second guide rail 32.

Therefore, the moving carriage 40 may move in the first direction D1 with the second guide rail 32 and move along the second guide rail 32 in the second direction D2. The controller 41, which is configured to generate a control signal which corresponds to a measurement result of a measurement unit (also referred to herein as a "measurer") 126 and to transmit the generated control signal to the motor 110, may be provided in the moving carriage 40.

The post frame 50 is fixed in the moving carriage 40 and is positioned below the moving carriage 40. The post frame 50 may include a plurality of posts 51, 52, 53, 54 and 55.

The plurality of posts 51, 52, 53, 54 and 55 are foldably and/or nestably and/or collapsibly connected so that a length of the post frame 50 may increase or decrease in a vertical direction of the laboratory while being fixed in the moving carriage 40.

A third direction D3 is defined as a direction in which the length of the post frame 50 increases or decreases. Therefore, the third direction D3 may be orthogonal to both the first direction D1 and the second direction D2.

The radiographic imaging unit 70 is a unit configured to radiate X-rays onto the object.

The radiographic imaging unit 70 may include an X-ray tube 71 configured to generate X-rays and a collimator 72 configured to guide the generated X-rays toward the object. A collision sensor 73 which is capable of detecting a collision may be provided in the X-ray tube 71, as illustrated in FIGS. 2 and 3. A position of the collision sensor 73 illustrated in FIGS. 2 and 3 is only an example, and the collision sensor 73 may be provided in another position.

A rotary joint 60 is arranged between the radiographic imaging unit 70 and the post frame 50.

The rotary joint 60 enables the radiographic imaging unit 70 to be coupled to the post frame 50 and supports a load applied to the radiographic imaging unit 70.

The rotary joint 60 may include a first rotary joint (also referred to herein as a "first rotary joint member") 61 connected to the lower post 51 of the post frame 50 and a second rotary joint (also referred to herein as a "second rotary joint member") 62 connected to the radiographic imaging unit 70.

The first rotary joint 61 is rotatably provided around a central axis of the post frame 50 that extends in the vertical direction of the laboratory. Therefore, the first rotary joint 61 may rotate on a plane which is perpendicular to the third direction D3. In this case, a rotation direction of the first rotary joint 61 may be newly defined. A newly defined fourth direction D4 is a rotation direction of an axis which is parallel to the third direction D3.

The second rotary joint 62 is rotatably provided on a plane which is perpendicular to the ceiling of the laboratory. Therefore, the second rotary joint 62 may rotate in a rotation direction of an axis which is parallel to the first direction D1 or the second direction D2. In this case, the rotation direction of the second rotary joint 62 may be newly defined. A newly defined fifth direction D5 is a rotation direction of an axis that extends in the first direction or the second direction.

The radiographic imaging unit 70 may be connected to the rotary joint 60 and rotate in the fourth direction D4 and the fifth direction D5. Further, the radiographic imaging unit 70 may be connected to the post frame 50 by the rotary joint 60 and linearly move in any one or more of the first direction D1, the second direction D2 and the third direction D3.

In order to cause movement of the radiographic imaging unit 70 in any of the first direction D1 to the fifth direction D5, the motor 110 may be provided. The motor 110 may be a motor that is electrically driven, and the motor 110 may include an encoder.

The motor 110 may include first, second, third, fourth and fifth motors (also referred to herein as "motor components") 111, 112, 113, 114 and 115 which respectively correspond to each direction D1, D2, D3, D4, and D5.

Each of the motors 111, 112, 113, 114 and 115 may be arranged in any of various positions in consideration of convenience of a design. For example, the first motor 111, which is configured to move the second guide rail 32 in the first direction D1, may be arranged near the first guide rail 31, the second motor 112, which is configured to move the moving carriage 40 in the second direction, may be arranged near the second guide rail 32, and the third motor 113, which is configured to increase or decrease the length of the post frame 50 in the third direction D3, may be arranged inside the moving carriage 40. In addition, the fourth motor 114, which is configured to rotatably move the radiographic imaging unit 70 in the fourth direction D4, may be arranged near the first rotary joint 61, and the fifth motor 115, which is configured to rotatably move the radiographic imaging unit 70 in the fifth direction D5, may be arranged near the second rotary joint 62.

Each motor 110 may be connected to a power transmission device (not illustrated) in order to cause translational and/or rotational movement of the radiographic imaging unit 70 in the first direction D1 to the fifth direction D5. The power transmission device (not illustrated) may include any one or more of a belt, a pulley, a chain, a sprocket, a shaft or the like that is commonly used.

The operating panel 80 that provides an interface configured to input various pieces of information which relate to X-ray imaging and to operate various devices is provided in a side of the radiographic imaging unit 70.

As illustrated in FIG. 4, the operating panel 80 may include a button 84 which is usable for operating a device, a display 81 that provides an interface configured to input various pieces of information which relate to X-ray imaging or to operate each device, and the handgrip 82 that may be gripped by the user. Further, the operating panel 80 may include a collision sensor 91 which is capable of detecting a collision, as illustrated in FIG. 4.

When the radiographic imaging apparatus captures the object, the display 81 of the operating panel 80 may provide a preview function of displaying the captured image such that an operator may immediately check the captured image. The captured image is displayed on the display 81 of the operating panel 80 in addition to a workstation. Accordingly, the operator may immediately check the captured image in any of the workstation and the operating panel 80.

The display 81 includes a touch screen via which a touch gesture of the operator may be input. Buttons in the form of soft keys that perform the same function as all physical buttons 84 for operating the device may be implemented in the touch screen. When the operator touches the button implemented in the touch screen, it is possible to input the same command as when the physical button is operated.

The button 84 may include rotation selecting buttons 85 and 86 that are operable by the user in order to rotate the radiographic imaging unit 70 in the fourth or fifth direction.

In order to rotate the radiographic imaging unit 70 in the fourth direction, the user may press the fourth direction rotation selecting button 85 and then rotate the radiographic imaging unit 70 in the fourth direction, or rotate the radiographic imaging unit 70 in the fourth direction while pressing the fourth direction rotation selecting button 85.

In order to rotate the radiographic imaging unit 70 in the fifth direction, the user may press the fifth direction rotation selecting button 86 and then rotate the radiographic imaging unit 70 in the fifth direction, or rotate the radiographic imaging unit 70 in the fifth direction while pressing the fifth direction rotation selecting button 86. Positions of the rotation selecting buttons 85 and 86 illustrated in the drawing are only examples, and may be changed. A button in the form of a soft key that performs the same function as the rotation selecting button may also be implemented in the touch screen.

While the drawing illustrates that the handgrip 82 is provided at a lower part of the operating panel 80, this is only an example, and the handgrip 82 may be provided in another position of the operating panel 80.

The user may grip the handgrip 82 of the operating panel 80 and thereby apply force or torque in order to move the radiographic imaging unit 70. Movement of the radiographic imaging unit 70 by the user will be described below.

A radiographic imaging apparatus 1 includes the controller 41 that is electrically connected to devices included in the radiographic imaging apparatus 1, such as the motor 110 and the operating panel 80, and controls each of the devices. The controller 41 may be provided inside the moving carriage 40, but the exemplary embodiments are not limited thereto, and the controller 41 may also be provided inside the operating panel 80.

The controller 41 drives each motor 110 in order to move the radiographic imaging unit 70 to a desired position.

For example, when the user inputs a desired imaging position via the operating panel 80, the controller 41 operates the motor 110 necessary for moving the imaging unit based on information on a current position and the input imaging position. According to the operation of the motor 110, the radiographic imaging unit 70 automatically moves to the imaging position desired by the user. This is referred to as an automatic movement mode. The user may activate the automatic movement mode remotely by using a remote controller (not illustrated) that includes an interface via which a command for moving the radiographic imaging unit 70 to a desired position may be input. In addition, the user may input a command for activating the automatic movement mode via the operating panel 80 or the workstation.

Further, the disclosed exemplary embodiment provides a power-assisted mode in which, when a user directly applies force or torque in order to move the radiographic imaging unit 70, the user's force or torque is detected and the motor 110 is operated to correspond thereto. In the power-assisted mode, the user may move the radiographic imaging unit 70 with less force or torque with assistance from the driving force of the motor 110.

A mode switching unit (also referred to herein as a "mode switcher") 83 may be provided in order to change the automatic movement mode to the power-assisted mode. The mode switching unit 83 may be provided in the form of a switch in the handgrip 82 of the operating panel 80. When the user presses the mode switching unit 83 by gripping the handgrip 82, the automatic movement mode may be changed to the power-assisted mode, and when the user releases the handgrip 82, the power-assisted mode may be changed to the automatic movement mode. In addition, even when the user applies force or torque to the imaging unit without gripping the handgrip 82, that is, without pressing the mode switching unit 83, the controller 41 may calculate the required amount of force or torque by using an algorithm to be described and change the automatic movement mode to the power-assisted mode.

In order for the user to directly move a position of the radiographic imaging unit 70, since frictional force generated in the vicinity of each motor 110 should be overcome, a relatively large amount of force or torque is necessary. However, in the power-assisted mode according to the disclosed exemplary embodiment, a user's force or torque is detected and the motor 110 is operated to correspond thereto, so that the user may move the radiographic imaging unit 70 with less force or torque In order to directly measure such force and torque, a sensor, such as a force/torque sensor, may be used. However, when the sensor is used, since a member necessary for installing the sensor, wiring for an input and output of a signal, and the like should be installed in addition to the sensor, a cost price of a product increases.

Therefore, the radiographic imaging apparatus according to the disclosed exemplary embodiment does not directly measure force or torque applied to the imaging unit by the user using a separate sensor, but indirectly calculates the amount of force or torque via the controller 41 and drives the motor 110. A method of the controller 41 calculating an amount of external force to be applied to the imaging unit will be described below.

In order to assist with translational movement of the radiographic imaging unit 70, the controller 41 configures the motor 110 for moving the radiographic imaging unit 70 in a direction corresponding to a direction of the calculated external force, and generates a control signal for controlling driving of the determined motor 110.

In order to generate a control signal for assisting with the translational movement of the radiographic imaging unit 70, the controller 41 may use force applied in three directions which are mutually perpendicular to each other and torque applied using at least one direction of the three directions as an axis in the calculated external force.

While the radiographic imaging unit 70 does not move, the motor 110 is coupled to a driving roller while driving is stopped. In order to manually move the radiographic imaging unit 70 to a desired position, a clutch which is configured for separating the motor 110 and the driving roller is necessary. In addition, in order to stop movement of the radiographic imaging unit 70, a separate brake is also necessary. When devices for implementing additional functions outside of a core function of the radiographic imaging apparatus, such as the clutch and the brake, are configured together in manufacture of the radiographic imaging apparatus, manufacture of the radiographic imaging apparatus becomes relatively complicated.

In the disclosed exemplary embodiment, the controller 41 calculates an amount of force applied to the radiographic imaging unit 70, drives the motor 110 to correspond thereto, and thus assists the radiographic imaging unit 70 in moving in a direction in which force is applied. In this aspect, the calculation of the amount of force applied to the radiographic imaging unit 70 may include any one or more of an amount and/or a direction of force, an amount and/or a direction of torque, an amount and/or a direction of linear momentum, and an amount and/or a direction of angular momentum. According to the disclosed exemplary embodiment, there is an advantage in that a component such as the clutch or the brake necessary for simply and manually moving the radiographic imaging unit 70 may be omitted. More specifically, installation of three clutches and brakes necessary for translational movement in three directions which are mutually perpendicular to each other may be omitted.

In order to assist with rotational movement of the radiographic imaging unit 70, the controller 41 configures the motor 110 for rotating the radiographic imaging unit 70 in a direction corresponding to a direction of the calculated external force, and generates a control signal for controlling driving of the determined motor 110.

In order to generate a control signal for assisting with the rotation movement of the radiographic imaging unit 70, the controller 41 may use force applied in three directions which are mutually perpendicular to each other and torque applied in at least two directions of the three directions using an axis in the calculated external force. In the disclosed exemplary embodiment, since a direction in which the radiographic imaging unit 70 may rotate includes two directions, that is, D4 and D5, a calculation value of torque applied in directions corresponding to D4 and D5 may be primarily used among directions of torque that are actually determined by the controller 41.

While the radiographic imaging unit 70 does not rotate, the motor 110 is coupled to the driving roller while driving is stopped. Therefore, in order to manually rotate the radiographic imaging unit 70, a clutch for separating the motor 110 and the driving roller is necessary. In addition, in order to stop rotation of the radiographic imaging unit 70, a separate brake is also necessary. As described above, when devices for implementing additional functions outside the core function of the radiographic imaging apparatus, such as the clutch and the brake, are configured together, manufacture of the radiographic imaging apparatus becomes relatively complicated.

In the disclosed exemplary embodiment, the controller 41 calculates an amount of torque applied to the radiographic imaging unit 70, drives the motor 110 to correspond thereto, and thus assists the radiographic imaging unit 70 in rotating in a direction in which torque is applied. According to the disclosed exemplary embodiment, there is an advantage in that a component such as the clutch or the brake necessary for simply and manually rotating the radiographic imaging unit 70 may be omitted. More specifically, two clutches and brakes necessary for rotating the radiographic imaging unit 70 in the directions D4 and D5 may not be installed.

As in the disclosed exemplary embodiment, when the controller 41 indirectly calculates an amount of force or torque applied to the radiographic imaging unit 70, drives the motor 110 to correspond thereto, and thus assists the radiographic imaging unit 70 in moving and/or rotating in a direction in which force or torque is applied, five clutches or brakes necessary for simply and manually moving or rotating the radiographic imaging unit 70 may not be installed. In addition, a sensor required when force or torque applied to the radiographic imaging unit 70 is directly measured need not be installed.

As another exemplary embodiment, when an amount of force necessary for the user to rotate the radiographic imaging unit 70 is less than an amount of force necessary for the user to translate the radiographic imaging unit 70 and the user does not feel a heavy burden, it may be implemented such that only assistance with the translational movement of the radiographic imaging unit 70 is provided and assistance with rotation is not provided. In this case, clutches and brakes that may be omitted when assistance with rotation of the radiographic imaging unit 70 is provided are required to be installed.

When there is no assistance from the motor 110 for translation and rotation of the radiographic imaging unit 70, since the user should translate and rotate the imaging unit by using his or her own force, the user should apply a larger amount of force than when there is assistance from the motor 110. When there is no assistance from the motor 110 in this manner, it is common for handgrips to be provided at both sides of the operating panel 80 such that the user may move the radiographic imaging unit 70 with both of his or her hands.

However, as in the disclosed exemplary embodiment, when assistance with translation and rotation of the radiographic imaging unit 70 is provided in the power-assisted mode, since the radiographic imaging unit 70 may be translated and rotated with a relatively small amount of force, the handgrip 82 of the operating panel 80 may have a form that may be gripped by one hand as illustrated in FIG. 4. Accordingly, since a space occupied by the handgrip 82 in the operating panel 80 decreases, it is possible to form the display 81 to be larger. Since the user may check more information at the same time without an additional operation via the larger display 81, it is possible to decrease a time taken for operating the device.

As described above, in the power-assisted mode, the user may easily move the radiographic imaging unit 70 in a desired direction. In particular, when the user moves the radiographic imaging unit 70 while pressing the mode switching unit 83 by gripping the handgrip 82, the power-assisted mode is activated, regardless of a movement direction of the radiographic imaging unit 70, and assists with the movement of the radiographic imaging unit 70.

The disclosed exemplary embodiment provides a function in which the power-assisted mode may be activated only when the radiographic imaging unit 70 moves in a specific direction. The operating panel 80 may include a button that may activate the power-assisted mode only when the radiographic imaging unit 70 moves in any one direction of the first direction, the second direction, and the third direction.

When the user applies force to move the radiographic imaging unit 70 in a corresponding direction while pressing a specific direction movement button 87, 88 or 89, the controller 41 calculates an amount of force applied to the radiographic imaging unit 70. The controller 41 operates the motor 110 which is configured to provide driving force to move the imaging unit in a direction of the calculated force, and thus assists with movement of the radiographic imaging unit 70.

For example, when the user moves the radiographic imaging unit 70 in the first direction while pressing the first direction movement button 87, the controller 41 drives only the motor 110 which is configured to output driving force for a first direction movement of the radiographic imaging unit 70, and activates the power-assisted mode only for the first direction movement. When the user moves the radiographic imaging unit 70 in another direction while pressing the first direction movement button 87, since the motor 110 which is configured to provide driving force for moving the radiographic imaging unit 70 in a direction other than the first direction is not driven, the motor 110 is unable to receive assistance of the power-assisted mode when the radiographic imaging unit 70 moves. The user may release the first direction movement button 87 and release activation of the power-assisted mode only for the first direction. This is similar to operations of the movement buttons 88 and 89 in other directions.

As illustrated in FIG. 4, the operating panel 80 may include each of the first direction, second direction and third direction movement buttons 87, 88 and 89. When the user operates the desired movement buttons 87, 88 and 89, the power-assisted mode may be activated only when the radiographic imaging unit 70 moves in a desired direction from among the first direction, the second direction, and the third direction. As illustrated in FIG. 4, the movement buttons 87, 88 and 89 may be implemented in the form of hard keys or may be implemented in the form of soft keys in the display 81. The above-described first direction, second direction, and third direction are only an example, and exemplary embodiments are not limited thereto. A movement button for a specific direction that may be generated by a combination of the first direction, the second direction, and the third direction may also be provided.

Figure 5:
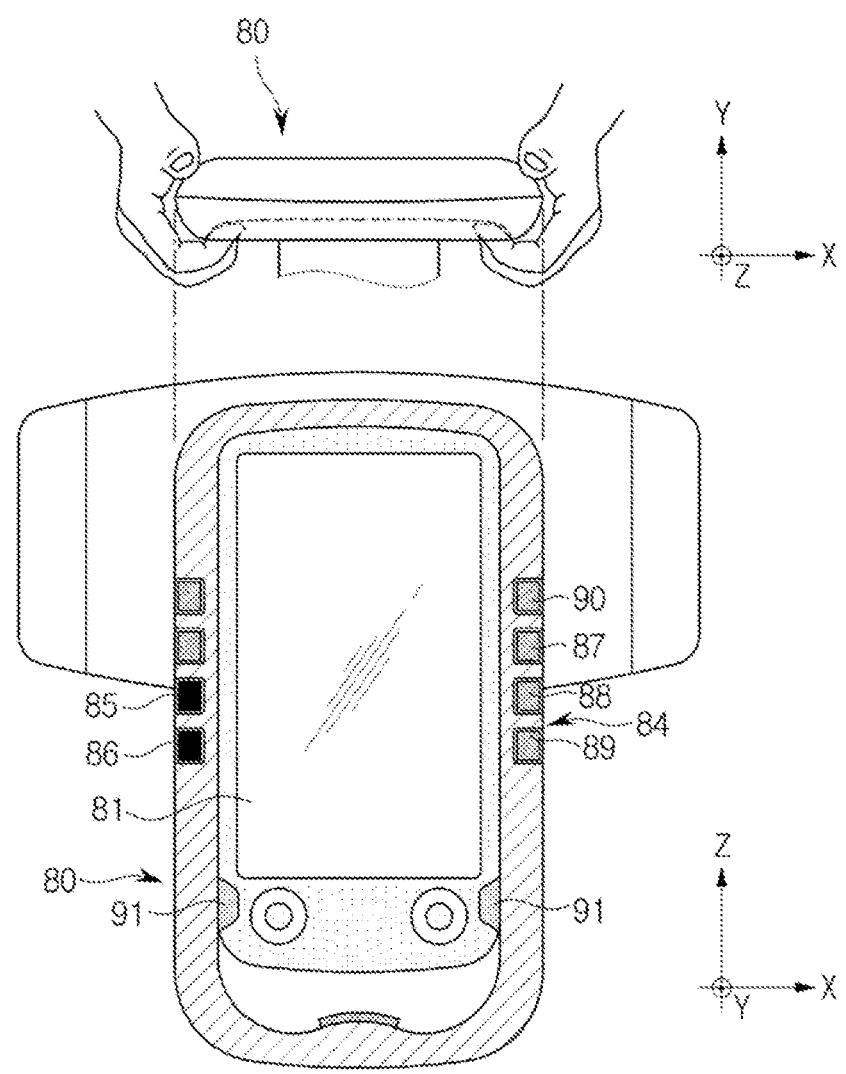
FIG. 5 is a diagram illustrating a state in which an operating panel is gripped, according to an exemplary embodiment.

FIG. 5 illustrates a method for gripping the operating panel 80 while pressing the movement buttons 87, 88 and 89. As illustrated in FIG. 5, in order for the user to grip the operating panel 80 more stably, a groove in which the user's finger may be stably positioned may be provided on a rear surface of the operating panel 80. As illustrated in FIG. 5, the user may grip the operating panel 80 while pressing the movement buttons 87, 88 and 89 and thereby move the radiographic imaging unit 70.

When the movement buttons 87, 88 and 89 are operated, the above function may be set to be performed while the movement buttons 87, 88 and 89 are pressed, but the exemplary embodiments are not limited thereto. When the movement buttons 87, 88 and 89 are pressed once, without maintaining the pressed state, the function may be implemented to be performed the same as when the buttons remain pressed. In this case, when the button is pressed once again, it is possible to release the power-assisted mode for one direction movement.

Further, the operating panel 80 may include a home position button 90 that is used to restore the imaging unit to a position that is previously designated by the user. The home position button may be implemented in the form of a hard key, as illustrated in FIG. 4, or may be implemented in the form of a soft key in the display 81. A position and a form of the home position button illustrated in FIG. 4 are only examples, and the home position button may also be provided in a different form in another position. When the user presses the home position button in the form of the hard key or touches the home position button in the form of the soft key, the imaging unit automatically moves to the pre-designated home position. The home position may be designated as any of various positions in advance and stored, and may be changed. When the home position button is operated, the controller 41 drives the motor 110 necessary for moving the imaging unit to the home position. When the imaging apparatus is positioned at the home position, the controller 41 stops driving of the motor 110 in order to stop a movement of the imaging apparatus at the home position.

Hereinafter, a process in which the controller 41 calculates force applied to the imaging unit and generates a control signal for assisting with translation and rotation of the radiographic imaging unit 70 based on the calculation result will be described in detail with reference to FIGS. 6A, 6B, 7A, 7B 8 and 9.

Figure 6A:
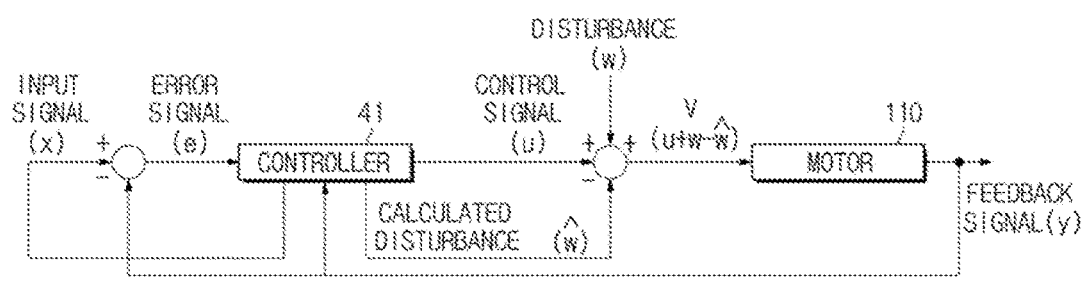
FIGS. 6A 6B, 7A, 7B and 8 are control block diagrams illustrating a radiographic imaging apparatus, according to an exemplary embodiment.
Figure 6B:
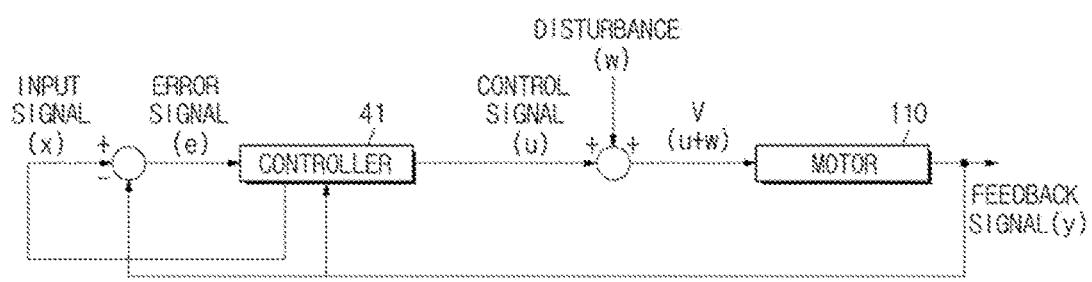

As illustrated in FIGS. 6A and 6B, the radiographic imaging apparatus according to the disclosed exemplary embodiment has no sensor which is configured to measure an amount of external force applied to the imaging unit. The controller 41 calculates a disturbance (w) applied to the radiographic imaging apparatus, converts this calculated disturbance into external force applied to the imaging unit, and thus indirectly measures external force. The controller may control any one or more of a position, a speed, a current, an acceleration, and/or an angular velocity of the motor based on a level and a direction of the external force that is calculated from the disturbance.

Figure 7A:
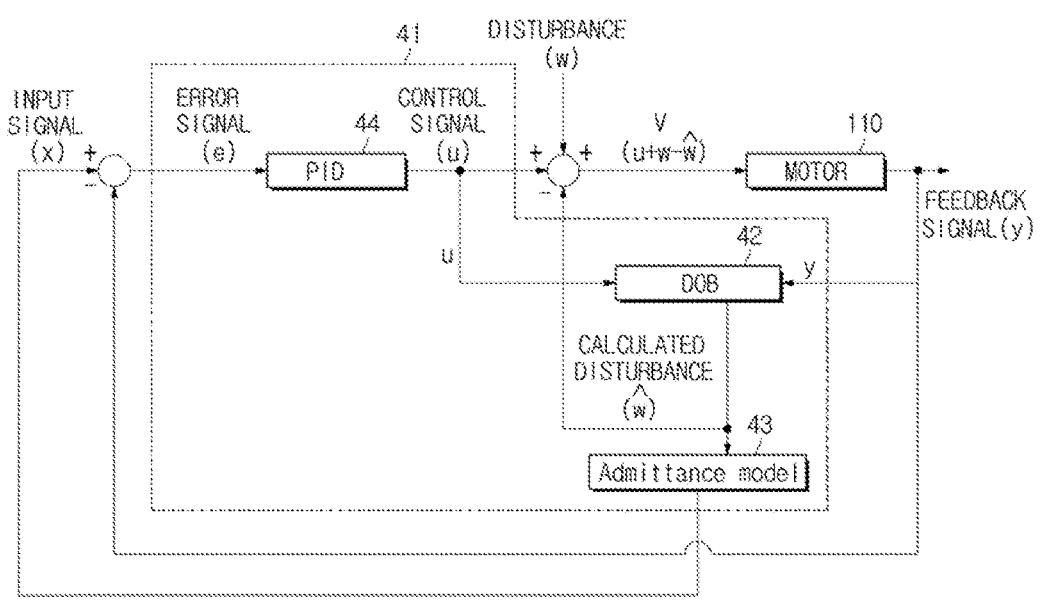
Figure 7B:
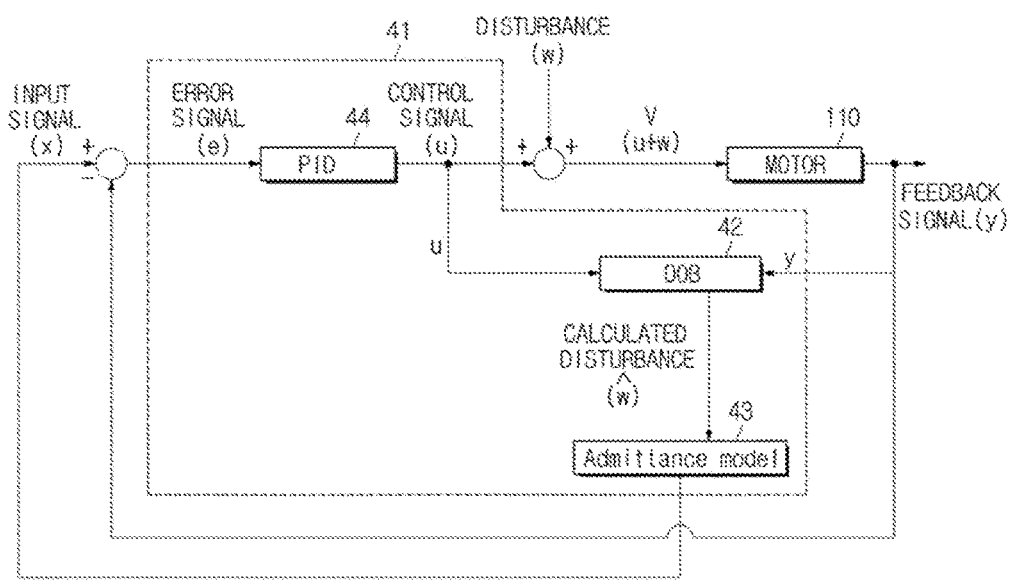

In view of the fact that external force applied to the imaging unit is included in the disturbance (w), the controller 41 calculates the disturbance, converts this calculated disturbance into external force applied to the imaging unit, and thus indirectly measures external force. As illustrated in FIGS. 7A and 7B, the controller 41 includes a disturbance observer (DOB) 42 capable of calculating disturbance. The disturbance observer 42 may be implemented in the controller 41 in the form of software, or may also be installed in the controller 41 as separate hardware.

Figure 8:
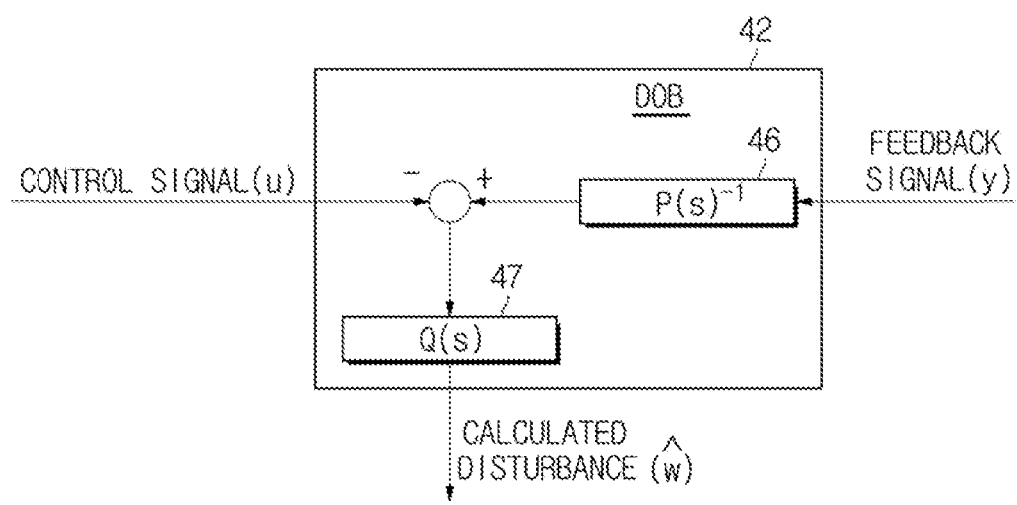

FIG. 8 illustrates a detailed configuration of the disturbance observer 42. The disturbance observer 42 calculates a disturbance (w) applied to the radiographic imaging apparatus by using a transfer function in which the motor 110 is modeled, or an inverse function $(P(s)^{-1})$ of a transfer function $(P(s))$ in which the motor 110 and a link and a driving joint connected to the motor 110 are modeled as one system. The transfer function of the motor may be represented by the following Equation 1.

$$P(s) = \frac{1}{\frac{J_m}{K_t}s^2 + \left(K_t + \frac{D_m R}{K_t}\right)s} \quad \langle \text{Equation 1} \rangle$$

In Equation 1, Jm denotes a moment of inertia of the motor 110, Kt denotes a torque constant of the motor 110, Dm denotes a damping coefficient of the motor 110, and R denotes an electrical resistance of the motor 110.

Since the numerator of the transfer function of the motor 110 or the inverse model of the system including the motor 110 has a greater order than the denominator, the function is unrealizable. Therefore, the disturbance observer 42 uses a Q filter (Q(s)) for realizing an inverse model of the motor 110 or the system including the motor 110. The Q filter is implemented as a low pass filter. When the Q filter is used, the inverse model of the motor 110 or the system including the motor 110 may be made as a realizable system. Further, the Q filter serving as the low pass filter generally blocks measurement noise that manifests as a high frequency component and passes disturbance that manifests as a low frequency component. Therefore, the disturbance observer 42 has a structure in which disturbance passed through the Q filter may be calculated and compensated. The Q filter may be represented by the following Equation 2.

$$Q(s) = \frac{\omega_n^2}{s^2 + 2\zeta\omega_n + \omega_n^2} \qquad \langle\text{Equation 2}\rangle$$

In Equation 2, ζ denotes a damping ration, and cod denotes a cutoff frequency.

Disturbance ($\hat{\omega}$) calculated by the disturbance observer 42 may be represented by the following Equation 3.

$$\hat{w} = yP(s)^{-1}Q(s) - uQ(s) \qquad \text{<Equation 3>}$$

In Equation 3, y denotes a feedback signal output from the motor 110, $P(s)^{-1}$ denotes a transfer function of an inverse model of the motor 110 or the system including the motor 110, Q(s) denotes a transfer function of the Q filter, and u denotes a control signal output from a proportional-integral-derivative controller 44 (hereinafter referred to as a "PID controller"). In an exemplary embodiment, the motor 110 may further include a feedback signal generator (not shown) configured to generate the feedback signal y based on the physical action of the motor 110. The feedback signal generator may be implemented, for example, as at least one from among a sensor configured to sense the physical action of the motor and a converter configured to convert motion information into an electrical signal.

Since a control signal input to the motor 110 includes an influence of disturbance (v=u+w), the feedback signal output from the motor 110 includes the influence of disturbance (y=P(s)u+P(s)w). When the control signal is subtracted (yP(s)$^{-1}$–u) from the feedback signal (yP(s)$^{-1}$) that has passed through the inverse model and includes the disturbance, and a signal in which the control signal is subtracted passes through the Q filter, the disturbance is calculated as (yP(s)$^{-1}$Q(s)–uQ(s)). The calculated disturbance may be removed from the control signal as shown in FIGS. 6A and 7A and also as in FIG. 10A to be described below, so that a control signal in which the disturbance is removed is transmitted to the motor 110. Alternatively, the calculated disturbance may not be removed from the control signal as shown in FIGS. 6B and 7B and also as in FIG. 10B to be described below. In this case, the control signal in which the disturbance is not removed may be transmitted to the motor 110.

This calculated disturbance includes force that is applied to the imaging unit by the user in order to move the imaging unit. The controller 41 maps a scale of the calculated disturbance to a scale of force or torque by applying a scale factor, and thus converts the calculated disturbance into force or torque. The controller 41 operates the motor 110 by using the force or torque converted in this manner, and thus assists with movement of the imaging unit. The controller 41 may include a band pass filter for removing an actual disturbance other than external force that is applied by the user in order to move the imaging unit, such as, for example, an oscillation of a device. The disturbance calculated by the disturbance observer 42 may pass through the band pass filter in order to directly remove an actual disturbance, or the actual disturbance may be removed by using a notch filter 45 to be described below.

As illustrated in FIGS. 7A and 7B, the controller 41 uses an admittance model 43 which uses the converted force or torque using an input, generates an input signal for controlling the motor 110, and transmits the generated input signal to the PID controller 44. The admittance model is an example of interaction control for controlling a subject of control that makes contact with a surrounding object. The admittance model is provided to control the position of a subject of control by using a force as an input, whereas an impedance model is provided to control a force of a subject of control by using the position as an input.

A transfer function (Y) of the admittance model 43 may be represented by the following Equation 4.

$$Y = \frac{X}{F} = \frac{1}{Ms^2 + Cs + K} \qquad \langle\text{Equation 4}\rangle$$

$$X = FY$$

$$\dot{X} = FsY$$

M denotes a mass coefficient of the admittance model 43, C denotes an attenuation coefficient of the admittance model 43, and K denotes a spring coefficient of the admittance model 43. F denotes force (or torque) converted from the disturbance calculated by the disturbance observer 42. X denotes a signal for controlling a position of the motor 110. $\dot{X}$ denotes a signal for controlling a speed of the motor 110. When disturbance is calculated, the controller 41 applies the calculated disturbance, that is, an external force applied to the imaging unit, to the admittance model 43, and calculates an input signal (X or $\dot{X}$) for controlling a position or a speed of the motor 110.

The controller 41 calculates an error signal (e) from the input signal (X) calculated through the admittance model 43 and the feedback signal (y) output from the motor 110, and calculates a control signal (u) for controlling the motor 110 by using the PID controller 44 that uses the calculated error signal (e) as an input. In order to calculate the control signal (u), the PID controller 44 may be used, or at least two of proportional control, integral control, and differential control may be combined and used.

According to the disclosed exemplary embodiment, when a gain of the PID controller 44 was set to be smaller than a gain tuned for minimizing an error, a control performance of the motor 110 using the disturbance observer 42 was improved. Therefore, the gain of the PID controller 44 may be set to have a value which is smaller than a predetermined threshold value, such as, for example, a preset optimal gain.

Communication between the controller 41 and the motor 110 of the radiographic imaging apparatus according to the disclosed exemplary embodiment supports CANopen communication profiles (industrial standard profiles DS-301, DS-305 and DS-402) based on a CAN communication interface. Communication between the controller 41 and the motor 110 may be performed through a CAN communication cable.

The motor 110 assists the radiographic imaging unit 70 in moving in a direction of external force that is indirectly calculated by using the disturbance observer 42 according to the control signal transmitted from the controller 41. Further, as illustrated in FIGS. 6, 7, and 8, the motor 110 may feed (y) information which relates to a driving speed or a position of the motor 110 back to the controller 41, and the controller 41 may update the control signal in real time based on the feedback signal in order to perform assistance more accurately.

As described above, the radiographic imaging apparatus according to the disclosed exemplary embodiment indirectly calculates an amount of external force applied to the imaging unit by using the disturbance observer 42. Accordingly, it is possible to provide the power-assisted mode for assisting with movement of the imaging unit without using the sensor. The user may move the radiographic imaging unit 70 with less force or torque in the power-assisted mode, and operation of the device may be less exhausting.

Figure 9:
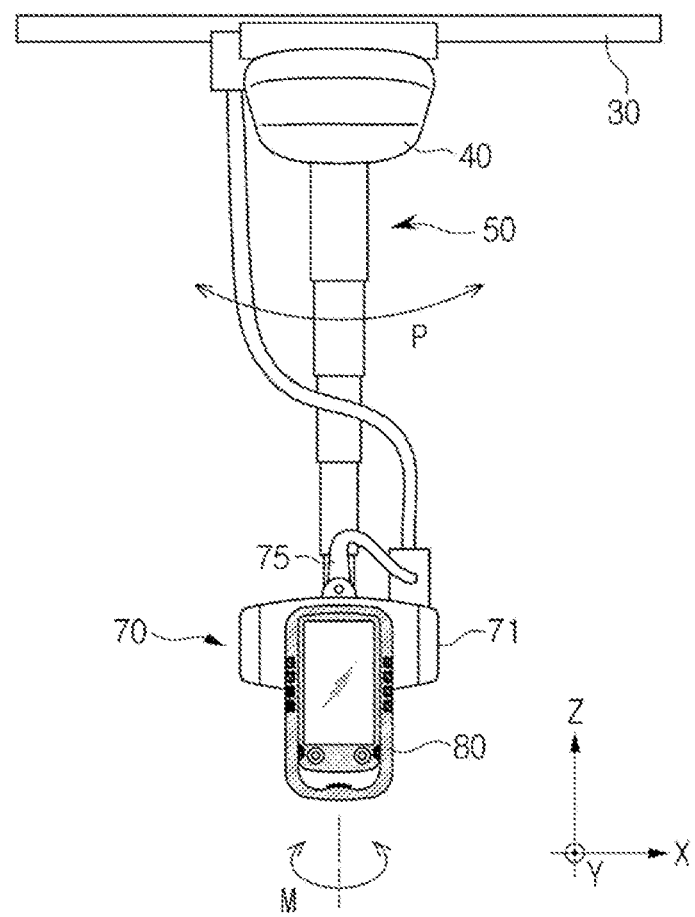
FIG. 9 is a diagram illustrating oscillation of a radiographic imaging apparatus, according to an exemplary embodiment.

Meanwhile, since the radiographic imaging apparatus has a structure in which the radiographic imaging unit 70 is installed at the ceiling through the post frame, simple pendulum oscillation may be generated, similar to a pendulum hanging by a thread. For example, when force is applied to move the radiographic imaging unit 70 in an x axis direction, the radiographic imaging unit 70 may generate a simple pendulum oscillation (P), as illustrated in FIG. 9. When this oscillation frequency matches a natural frequency of the device, an oscillation caused by resonance may be generated.

Further, as illustrated in FIGS. 2 and 3, the radiographic imaging unit 70 of the radiographic imaging apparatus according to the disclosed exemplary embodiment is not installed along an extension line of the post frame, but is connected to the rotary joint and installed outside of the extension line of the post frame. Therefore, a center of mass of the radiographic imaging unit 70 and a center of the post frame do not match. Since the center of mass of the radiographic imaging unit 70 and the center of the post frame do not match, as illustrated in FIG. 9, the radiographic imaging unit 70 may generate a rotational oscillation (M) with respect to the post frame, which serves as a rotation axis. For example, when force is applied to move the radiographic imaging unit 70 in an x axis direction, the radiographic imaging unit 70 may generate a rotational oscillation, as illustrated in FIG. 9. When this oscillation frequency matches a natural frequency of the device, an oscillation caused by resonance may be generated.

When an oscillation phenomenon due to resonance is generated, it may be difficult to position the device at a desired position accurately, structural fatigue may accumulate in the device, or the device may be damaged.

Accordingly, in the disclosed exemplary embodiment, a signal of a frequency band which corresponds to a resonance frequency band of the radiographic imaging apparatus is removed from the control signal by using the notch filter 45 represented by the following Equation 5. Therefore, generation of an oscillation caused by resonance is suppressed. The notch filter 45 is only an example and other band pass filters may also be used.

$$N(s) = \frac{s^2 + \omega_0^2}{s^2 + \frac{\omega_0}{Q}s + \omega_0^2} \quad \langle \text{Equation 5} \rangle$$

Equation 5 denotes a transfer function of the notch filter 45, $\omega_o$ denotes a notch frequency including a resonance frequency to be removed of the radiographic imaging apparatus, Q denotes a quality factor, and a stop bandwidth to be removed through the notch filter 45 is determined as a ratio of the notch frequency to the quality factor, that is, $\omega_o/Q$.

Figure 10A:
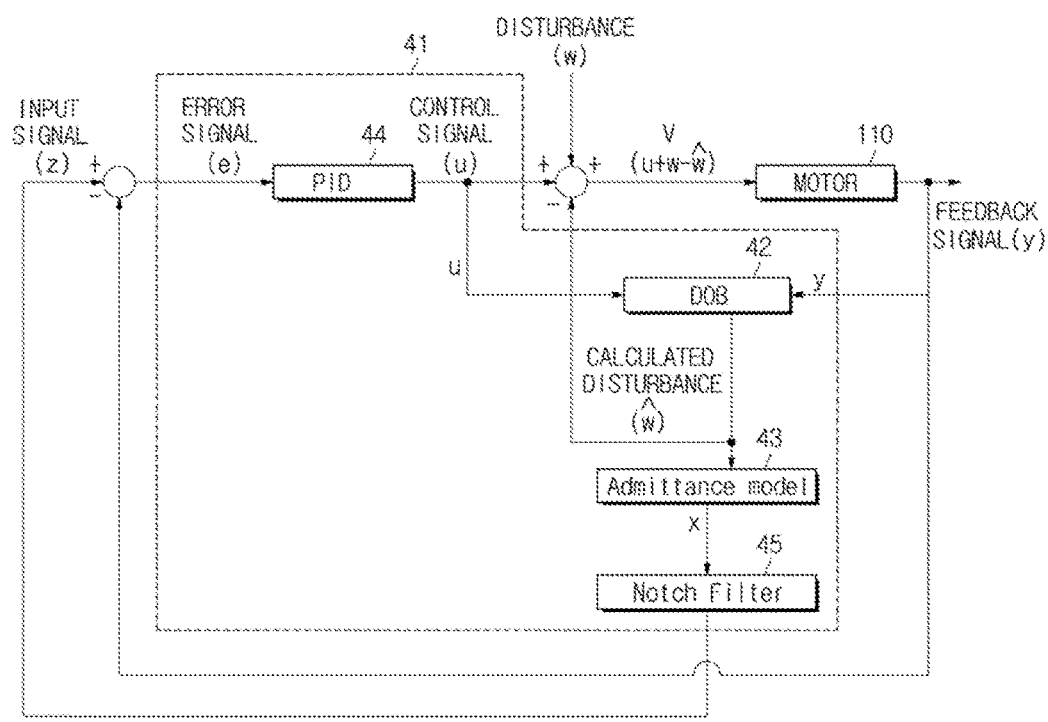
FIGS. 10A and 10B are control block diagrams of a radiographic imaging apparatus for decreasing oscillation of the radiographic imaging apparatus.
Figure 10B:
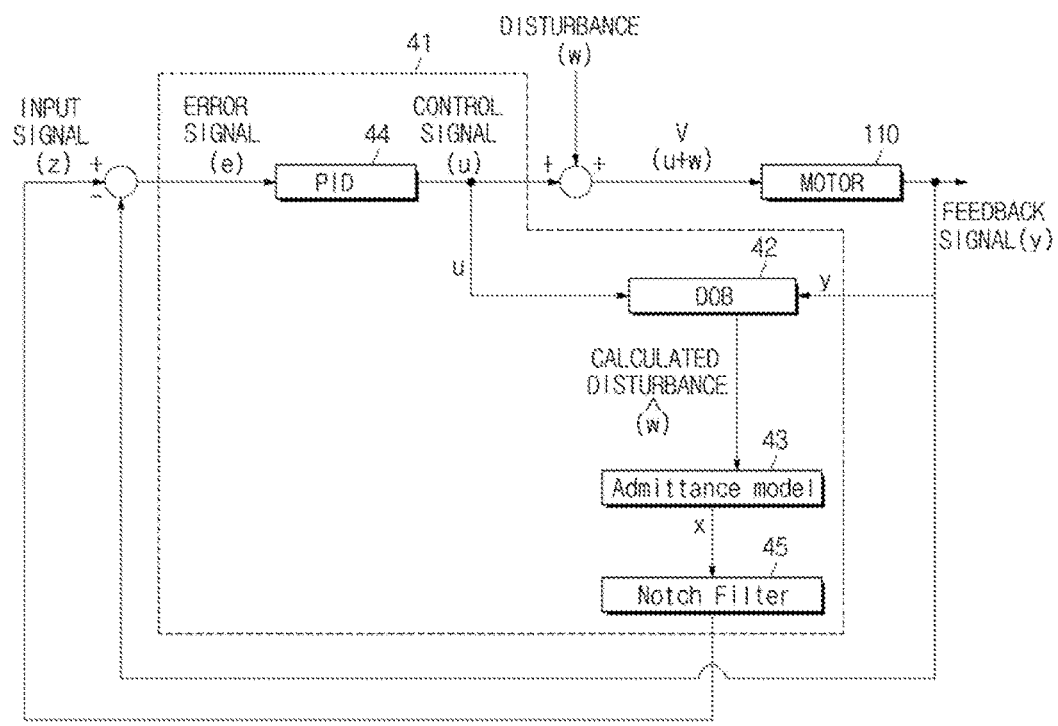

As illustrated in FIGS. 10A and 10B, a signal (x) output from the admittance model 43 is not directly input to the PID controller 44, but propagates through the notch filter 45. By propagating through the notch filter 45, a signal of the resonance frequency band of the imaging unit is removed. An input signal (z) calculated by using the notch filter 45 becomes an input signal of the PID controller 44.

In the disclosed exemplary embodiment, in order to efficiently remove the resonance frequency by using the notch filter 45, a lookup table (LT) in which the natural frequency of the radiographic imaging apparatus that may be varied according to a position of the radiographic imaging unit 70 is mapped to a space in which the radiographic imaging unit 70 may move may be stored in advance. The controller 41 determines a natural frequency of the radiographic imaging apparatus which corresponds to a movement position by using the lookup table (LT) whenever the radiographic imaging unit 70 moves, applies the notch filter 45, and removes a signal of a frequency band which corresponds to the resonance frequency band from an input signal (x).

Figure 11:
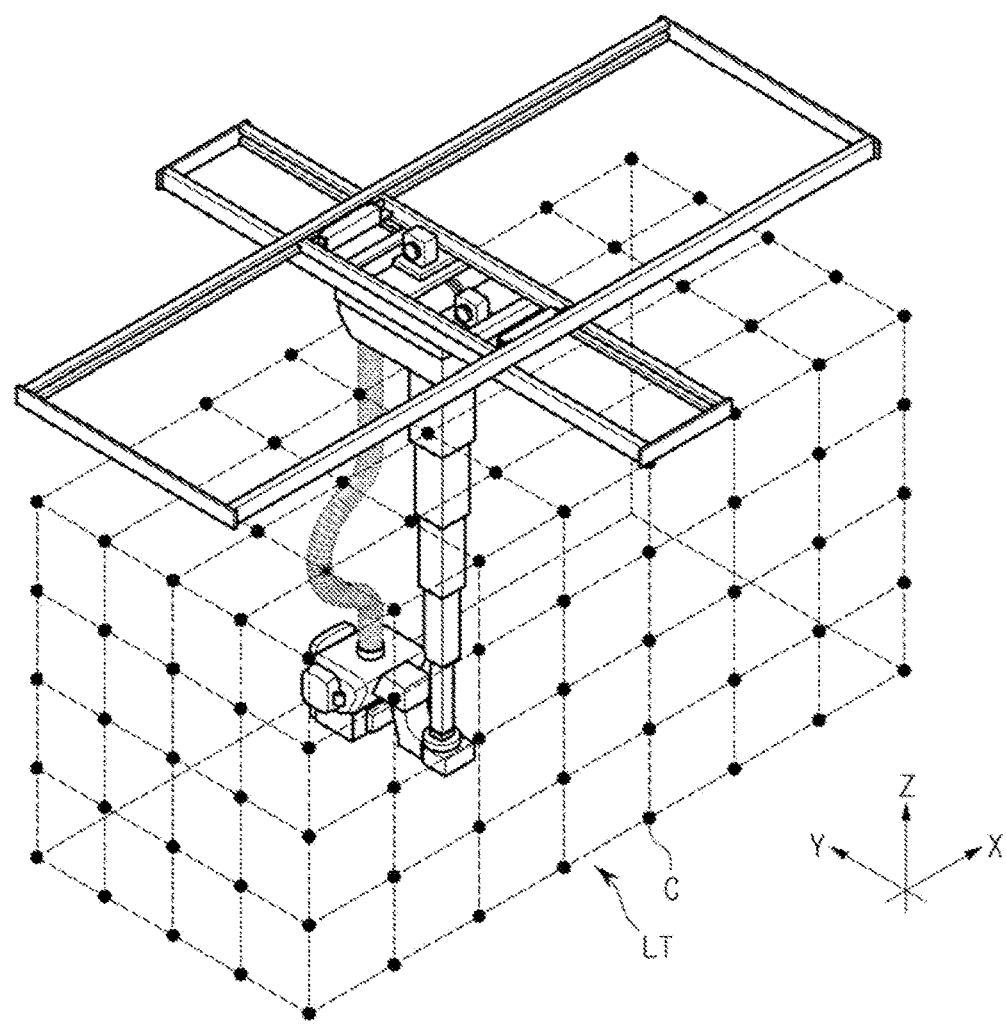
FIG. 11 is a diagram illustrating a concept in which a resonance frequency lookup table of a radiographic imaging apparatus according to an exemplary embodiment is mapped to a virtual 3D space that represents a range of movement of the radiographic imaging apparatus.

FIG. 11 is a diagram illustrating a concept of a lookup table (LT) in which a natural frequency of the radiographic imaging unit 70 is mapped to a main point (C) of a 3D virtual space which corresponds to a space within which the radiographic imaging unit 70 may move. The natural frequency may be mapped as a different value for each main point (C) of the 3D virtual space. For example, since a frequency of the simple pendulum oscillation becomes greater as the post frame becomes shorter, a value of the natural frequency may increase as it approaches the ceiling.

The lookup table (LT) that is completed in consideration of the natural frequency of the radiographic imaging apparatus that may be varied according to a characteristic of the oscillation in this manner may be stored in the controller 41. The controller 41 uses the lookup table (LT) to calculate the natural frequency of the radiographic imaging apparatus which corresponds to a movement position of the radiographic imaging unit 70 that is detected in real time.

In particular, when the radiographic imaging unit 70 moves, a potentiometer or an encoder of the motor 110 detects a position of the radiographic imaging unit 70, and transmits a change in the position of the radiographic imaging unit 70 to the controller 41 in real time. The controller 41 uses the lookup table (LT) to determine natural frequency values that are mapped to the closest points (C) in the vicinity of the position of the radiographic imaging unit 70 that is detected in real time, interpolates the natural frequency values, and calculates the natural frequency of the radiographic imaging apparatus that corresponds to the position of the radiographic imaging unit 70. The controller 41 applies this calculated natural frequency to the notch filter 45 and removes a signal of the resonance frequency band from the signal (x) calculated from the admittance model 43.

In the power-assisted mode, when the user moves the radiographic imaging unit 70 and wants to stop movement of the radiographic imaging unit 70 at a target position, it is difficult to stop movement of the radiographic imaging unit 70 accurately at the target position in a single attempt. In general, a movement speed of the radiographic imaging unit 70 is decreased near the target position, the position of the radiographic imaging unit 70 is finely adjusted, and the radiographic imaging unit 70 is positioned at the target position.

The radiographic imaging apparatus according to one or more exemplary embodiments may automatically stop the radiographic imaging unit 70 at the target position without finely adjusting the position of the radiographic imaging unit 70 near the target position, in order for the user to position the radiographic imaging unit 70 accurately at the target position.

In particular, when the movement speed of the radiographic imaging unit 70 is less than or equal to a preset speed at a preset specific position, the controller 41 stops driving of the motor 110 which is configured to assist with movement of the radiographic imaging unit 70, and stops the radiographic imaging unit 70 at the preset specific position. In this aspect, driving of the motor 110 is stopped without using a separate brake, and therefore movement of the radiographic imaging unit 70 is stopped. Hereinafter, a mode in which such a function is implemented is referred to as a virtual detent mode, and will be described in detail.

In the virtual detent mode, a position at which movement of the radiographic imaging unit 70 is automatically stopped may be directly designated and set by the user, or may be preset and stored as a position in which the radiographic imaging unit 70 is frequently positioned. Hereinafter, the above preset position is referred to as a stop position. The encoder or the potentiometer detects the position of the radiographic imaging unit 70 in real time and transmits the detected position to the controller 41. The controller 41 determines whether the detected position of the radiographic imaging unit 70 transmitted in real time matches the stop position.

Further, a speed sensor configured to detect a movement speed of the radiographic imaging unit 70 detects the movement speed of the radiographic imaging unit 70 in real time, and transmits the result to the controller 41. The controller 41 determines whether the detected movement speed of the radiographic imaging unit 70 transmitted in real time is less than or equal to the preset speed at the stop position. Hereinafter, the preset speed is referred to as a first reference speed. Since the user is considered to want to stop movement of the radiographic imaging unit 70 at the stop position when the speed of the radiographic imaging unit 70 is sufficiently low, the first reference speed may be determined in this regard.

When the detected position of the radiographic imaging unit 70 matches the stop position and the detected movement speed of the radiographic imaging unit 70 is less than or equal to the first reference speed, the controller 41 stops driving of the motor 110 which is configured to assist with movement of the radiographic imaging unit 70 and thereby facilitates a cessation of movement of the radiographic imaging unit 70 at the stop position.

According to another exemplary embodiment, the controller 41 may also determine whether a real time position of the radiographic imaging unit 70 transmitted from the encoder or the potentiometer enters a space (hereinafter referred to as a "stop space") which has a predetermined volume that includes the stop position. Further, when the position of the radiographic imaging unit 70 enters the stop space, the controller 41 determines whether the movement speed of the radiographic imaging unit 70 transmitted in real time is less than or equal to the first reference speed. When the movement speed of the radiographic imaging unit 70 is less than or equal to the first reference speed, the controller 41 decreases the movement speed of the radiographic imaging unit 70 such that the radiographic imaging unit 70 may stop at the stop position. When the stop space is set, the radiographic imaging unit 70 is not immediately stopped, but the radiographic imaging unit 70 may be stopped while decreasing the movement speed of the radiographic imaging unit 70. Therefore, the radiographic imaging unit 70 may be stopped at the stop position more smoothly.

An input device, such as, for example, a button which is capable of turning the above virtual detent mode on or off as necessary, may be provided in the operating panel 80 or the workstation. The user may operate the button to turn the virtual detent mode on, move the radiographic imaging unit 70 to the preset stop position, and adjust the movement speed of the radiographic imaging unit 70 to be less than or equal to the first reference speed at the stop position so that the radiographic imaging unit 70 may stop at the stop position. In addition, the radiographic imaging unit 70 may enter the stop space at a speed which is less than or equal to the first reference speed, and the radiographic imaging unit 70 may decelerate as it approaches the stop position and then stop at the stop position.

As another exemplary embodiment, when the radiographic imaging unit 70 approaches an end portion of the guide rail, in order to prevent the radiographic imaging unit 70 from deviating, the controller 41 may stop the motor 110 that is being operated regardless of whether the virtual detent mode is turned on or off or the movement speed of the radiographic imaging unit 70, and thereby stop movement of the radiographic imaging unit 70.

In the virtual detent mode, without using the brake to stop movement of the radiographic imaging unit 70, driving of the motor 110 is stopped in order to stop movement of the radiographic imaging unit 70. Therefore, it is possible to prevent noise or oscillation of the device that is generated when the brake is used. Further, the brake itself may be omitted.

In the power-assisted mode, when the user wants to stop movement of the radiographic imaging unit 70 at a target position while moving the radiographic imaging unit 70, it is difficult to stop movement of the radiographic imaging unit 70 accurately at the target position at a particular time. When the above virtual detent mode is not used, in general, a movement speed of the radiographic imaging unit 70 is decreased near the target position, the position of the radiographic imaging unit 70 is finely adjusted, and the radiographic imaging unit 70 is positioned at the target position.

In the power-assisted mode, a movement sensitivity of the radiographic imaging unit 70, that is, a ratio (velocity/force) of the movement speed of the radiographic imaging unit 70 to a force that is applied to move the radiographic imaging unit 70 may be set to be higher, such that the user may move the radiographic imaging unit 70 with less force. As the movement sensitivity increases, a level of force necessary for moving the radiographic imaging unit 70 at the same movement speed decreases. In the power-assisted mode, in this aspect, the movement sensitivity is set to easily move the radiographic imaging unit 70 with less force. Therefore, when the user applies less force in order to finely adjust the position of the radiographic imaging unit 70, the radiographic imaging unit 70 may move farther than a desired distance. Accordingly, there may be a problem in that it is difficult to finely adjust the position of the radiographic imaging unit 70.

Figure 12:
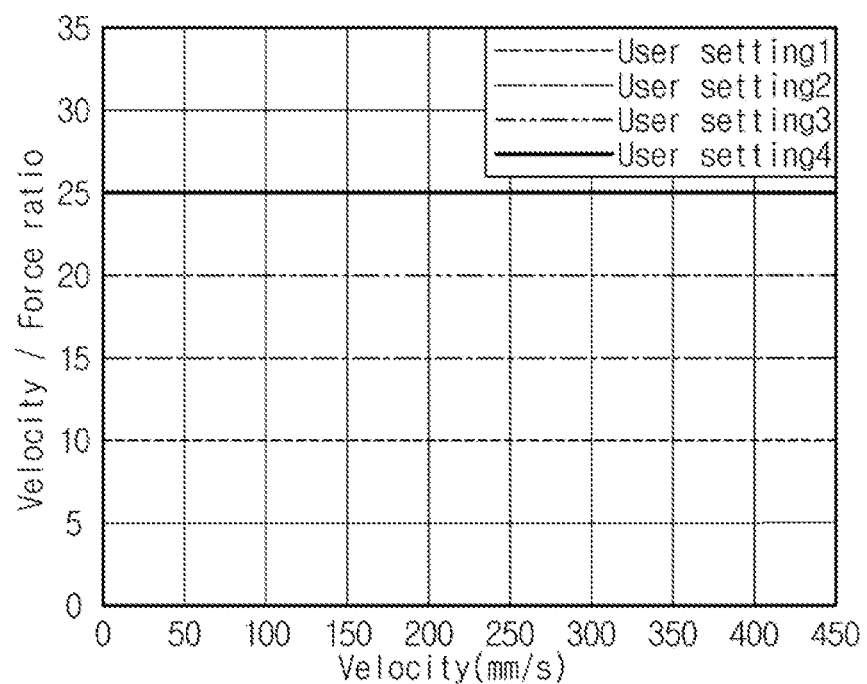
FIG. 12 shows the graph of a fixed movement sensitivity of a radiographic imaging apparatus, according to an exemplary embodiment.

FIG. 12 shows a fixed movement sensitivity. As the movement sensitivity increases, the user feels that the radiographic imaging unit 70 is relatively light when he or she moves the radiographic imaging unit 70. Conversely, as the movement sensitivity decreases, the user feels that the radiographic imaging unit 70 is relatively heavy when he or she moves the radiographic imaging unit 70. When the position of the radiographic imaging unit 70 needs to be finely adjusted, a low movement sensitivity is advantageous. This is because, when the position of the radiographic imaging unit 70 needs to be finely adjusted, a difference between a movement distance of the radiographic imaging unit 70 desired by the user and an actual movement distance of the radiographic imaging unit 70 should be small. However, when the radiographic imaging unit 70 moves a certain distance or more, a high movement sensitivity is advantageous. This is because it is important for force necessary for moving the radiographic imaging unit 70 to have a low level in this case.

As shown in FIG. 12, when the movement sensitivity is set to have a constant value, an amount of force which is necessary for obtaining the same movement speed decreases as a movement sensitivity value increases. Therefore, it is advantageous when the radiographic imaging unit 70 moves at least a certain distance. However, when the position of the radiographic imaging unit 70 is finely adjusted, since the radiographic imaging unit 70 may move farther than a distance desired by the user, it is disadvantageous. Conversely, when the movement sensitivity value decreases, it may be advantageous when the position of the radiographic imaging unit 70 is finely adjusted, but it may be disadvantageous when the radiographic imaging unit 70 moves at least a certain distance.

Figure 13:
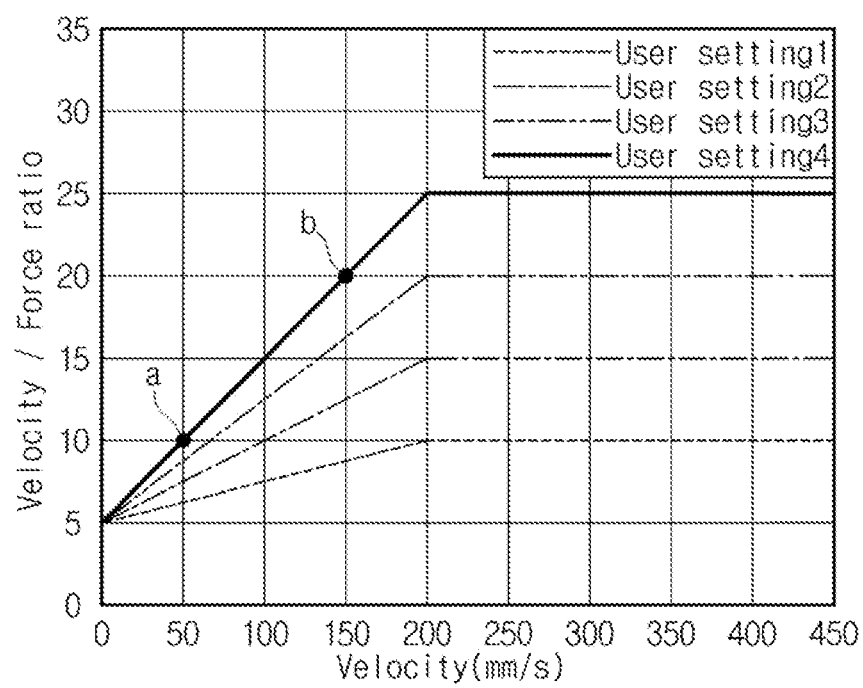
FIG. 13 shows the graph of a variable movement sensitivity of a radiographic imaging apparatus, according to an exemplary embodiment.

Therefore, in the disclosed exemplary embodiment, as shown in FIG. 13, a variable movement sensitivity is set, and settings appropriate for both when the radiographic imaging unit 70 moves and when the position of the radiographic imaging unit 70 is finely adjusted are provided.

In particular, as shown in FIG. 13, when the movement speed of the radiographic imaging unit 70 is greater than a preset second reference speed, for example, 200 mm/s, the movement sensitivity of the radiographic imaging unit 70 is fixed as a constant value, and settings favorable for movement of the radiographic imaging unit 70 are provided. When the movement speed of the radiographic imaging unit 70 is less than or equal to the preset second reference speed, the movement sensitivity is set to be decreased as the speed of the radiographic imaging unit 70 decreases, and settings favorable for fine adjustment of the radiographic imaging unit 70 are provided.

When the movement speed of the radiographic imaging unit 70 is less than or equal to the second reference speed, the movement sensitivity of the radiographic imaging unit 70 decreases as the movement speed of the radiographic imaging unit 70 decreases. Therefore, the user may precisely control the radiographic imaging unit. For example, in fine adjustment, a movement sensitivity (a) when the radiographic imaging unit 70 needs to be moved at a low speed is smaller than a movement sensitivity (b) when the radiographic imaging unit 70 needs to be moved at a slightly higher speed. Accordingly, even when the movement sensitivity value of the radiographic imaging unit 70 is small, the user may adjust the position of the radiographic imaging unit 70 more accurately than when the value is fixed.

Since the user is considered to want to finely adjust the position of the radiographic imaging unit 70 when the speed of the radiographic imaging unit 70 is sufficiently low, the second reference speed may be determined in this regard.

The variable movement sensitivity shown in FIG. 13 may be preset and stored in the controller 41. The user may select the fixed movement sensitivity shown in FIG. 12 to set the device, or may select the variable movement sensitivity shown in FIG. 13 in order to set the device.

An input device, such as, for example, a button which is capable of turning setting of the above variable movement sensitivity on or off as necessary, may be provided in the operating panel 80 or the workstation. The user may operate the button in order to set the variable movement sensitivity as necessary.

While the variable movement sensitivity is set, the speed sensor detects the movement speed of the radiographic imaging unit 70 in real time and transmits the result to the controller 41. The controller 41 adjusts the movement sensitivity according to a change in the speed of the radiographic imaging unit 70 as shown in FIG. 13 when the detected movement speed of the radiographic imaging unit 70 transmitted in real time is less than or equal to the second reference speed.

When the radiographic imaging unit 70 moves with assistance from the motor 110, the controller 41 outputs a signal sound which indicates movement of the radiographic imaging unit 70 via the sound output unit (also referred to herein as a "sound outputter" and/or as a "speaker") 49 and may inform the user of movement of the radiographic imaging unit 70 being performed with assistance from the motor 110.

A signal sound to be stored in connection with movement of the radiographic imaging unit 70 may be variably set and stored according to a movement method of the radiographic imaging unit 70. For example, a signal sound output when movement is performed according to the automatic movement mode and a signal sound output when movement is performed according to the power-assisted mode may be variably set and stored. Therefore, the user may know the current movement mode based on the output signal sound.

The sound output through the sound output unit 49 may be stored in advance in connection with movement of the radiographic imaging unit 70 and various operations of the radiographic imaging apparatus. For example, various types of camera shutter sounds may be stored in advance such that the camera shutter sound may be output when radiography of the radiographic imaging apparatus is performed. When radiography is actually performed, the camera shutter sound stored in advance may be output via the sound output unit 49.

Figure 14:
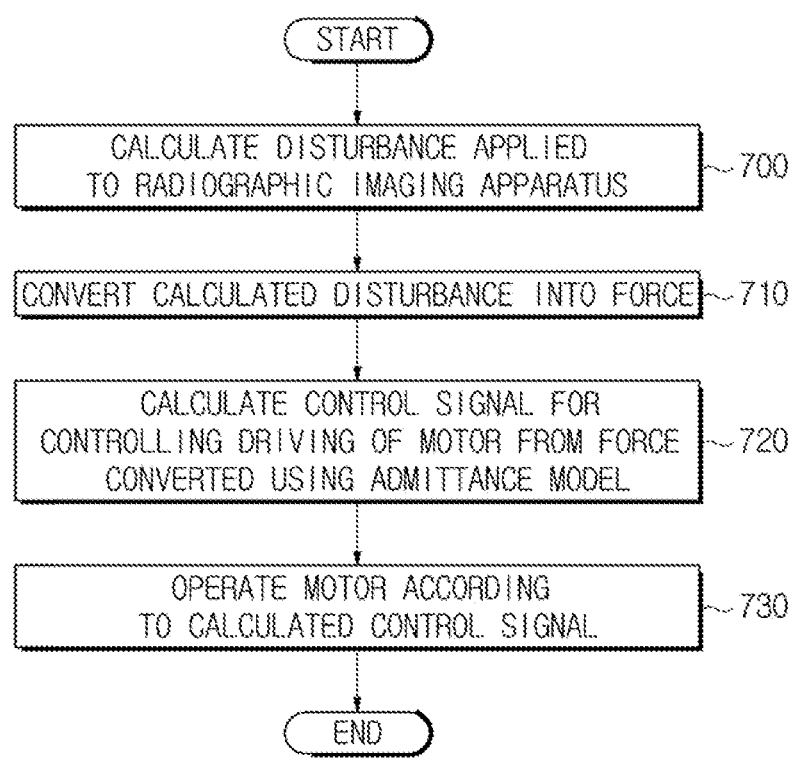
FIG. 14 is a flowchart illustrating a method for controlling a radiographic imaging apparatus, according to an exemplary embodiment.

FIG. 14 is a flowchart illustrating a method for controlling a radiographic imaging apparatus, according to an exemplary embodiment.

As illustrated in FIG. 14, in operation 700, the controller 41 calculates a disturbance applied to the radiographic imaging apparatus, and then, in operation 710, the controller 41 converts the calculated disturbance into force.

As illustrated in FIGS. 6A and 6B, the radiographic imaging apparatus according to the disclosed exemplary embodiment has no sensor that is configured to measure external force applied to the imaging unit. The controller 41 calculates a disturbance applied to the radiographic imaging apparatus, converts this calculated disturbance into external force applied to the imaging unit, and thus indirectly measures external force.

In view of the fact that external force applied to the imaging unit is included in the disturbance, the controller 41 calculates the disturbance, converts this calculated disturbance into external force applied to the imaging unit, and thus indirectly measures external force. As illustrated in FIGS. 7A and 7B, the controller 41 includes the disturbance observer (DOB) 42 which is capable of calculating a disturbance. The disturbance observer 42 may be implemented in the controller 41 in the form of software, or may also be installed in the controller 41 as separate hardware.

FIG. 8 illustrates a detailed configuration of the disturbance observer 42. The disturbance observer 42 calculates a disturbance (w) applied to the radiographic imaging apparatus by using a transfer function in which the motor 110 is modeled or an inverse function (P(s)$^{-1}$) of a transfer function (P(s)) in which the motor 110 and a link and a driving joint connected to the motor 110 are modeled as one system.

Since the numerator of the transfer function of the motor 110 or the inverse model of the system including the motor 110 has a greater order than the denominator, the function is unrealizable. Therefore, the disturbance observer 42 uses a Q filter (Q(s)) for realizing an inverse model of the motor 110 or the system including the motor 110. The Q filter is implemented as a low pass filter. When the Q filter is used, the inverse model of the motor 110 or the system including the motor 110 may be made as a realizable system. Further, the Q filter serving as the low pass filter generally blocks measurement noise that manifests as a high frequency component and passes disturbance that manifests as a low frequency component. Therefore, the disturbance observer 42 has a structure in which disturbance that passes through the Q filter may be calculated and compensated.

Disturbance (ŵ) calculated by the disturbance observer 42 may be represented by the following Equation 3.

$$\hat{w} = yP(s)^{-1}Q(s) - uQ(s) \qquad \text{<Equation 3>}$$

In Equation 1, y denotes a feedback signal output from the motor 110, P(s)$^{-1}$ denotes a transfer function of an inverse model of the motor 110 or the system including the motor 110, Q(s) denotes a transfer function of the Q filter, and u denotes a control signal output from the PID controller 44.

Since a control signal input to the motor 110 includes an influence of disturbance (v=u+w), the feedback signal output from the motor 110 includes the influence of disturbance (y=P(s)u+P(s)w). When the control signal is subtracted (yP(s)$^{-1}$−u) from the feedback signal (yP(s)$^{-1}$) that has passed through the inverse model and includes the disturbance, and a signal in which the control signal is subtracted passes through the Q filter, the disturbance is calculated (yP(s)$^{-1}$Q(s)−uQ(s)).

This calculated disturbance includes force that is applied to the imaging unit by the user in order to move the imaging unit. The controller 41 maps a scale of the calculated disturbance to a scale of force or torque by applying a scale factor, and thus converts the calculated disturbance into force or torque.

In operation 720, the controller 41 calculates a control signal for controlling driving of the motor 110 from force converted by using the admittance model 43, and operates the motor 110 according to the calculated control signal in operation 730.

As illustrated in FIGS. 7A and 7B, the controller 41 uses an admittance model 43 which uses the converted force or torque as an input, generates an input signal for controlling the motor 110 and transmits the signal to the PID controller 44. A transfer function (Y) of the admittance model 43 may be represented by the following Equation 4.

$$Y = \frac{X}{F} = \frac{1}{Ms^2 + Cs + K} \qquad \text{<Equation 4>}$$

$$X = FY$$

$$\dot{X} = FsY$$

M denotes a mass coefficient of the admittance model 43, C denotes an attenuation coefficient of the admittance model 43, and K denotes a spring coefficient of the admittance model 43. F denotes force (or torque) converted from the disturbance calculated by the disturbance observer 42. X denotes a signal for controlling a position of the motor 110. Ẋ denotes a signal for controlling a speed of the motor 110. When disturbance is calculated, the controller 41 applies the calculated disturbance, that is, external force applied to the imaging unit, to the admittance model 43, and calculates an input signal (X or Ẋ) for controlling a position or a speed of the motor 110.

The controller 41 calculates an error signal (e) from the input signal calculated through the admittance model 43 and the feedback signal output from the motor 110, and calculates a control signal for controlling the motor 110 using the PID controller 44 that uses the calculated error signal (e) as an input. In order to calculate the control signal, the PID controller 44 may be used or at least two of proportional control, integral control and differential control may be combined and used.

According to the disclosed exemplary embodiment, when a gain of the PID controller 44 was set to be smaller than a gain tuned for minimizing an error, control performance of the motor 110 using the disturbance observer 42 was improved. Therefore, the gain of the PID controller 44 may be set to have a value which is smaller than a preset optimal gain, or smaller than a predetermined threshold value.

Communication between the controller 41 and the motor 110 of the radiographic imaging apparatus according to the disclosed exemplary embodiment supports CANopen communication profiles (industrial standard profiles DS-301, DS-305 and DS-402) based on a CAN communication interface. Communication between the controller 41 and the motor 110 may be performed through a CAN communication cable.

The motor 110 assists the radiographic imaging unit 70 in moving in a direction of external force that is indirectly calculated using the disturbance observer 42 according to the control signal transmitted from the controller 41. Further, as illustrated in FIGS. 6A, 6B, 7A, 7B and 8, the motor 110 may feed (y) information which relates to a driving speed or a position of the motor 110 back to the controller 41, and the controller 41 updates the control signal in real time based on the feedback signal to perform assistance more accurately.

Figure 15:
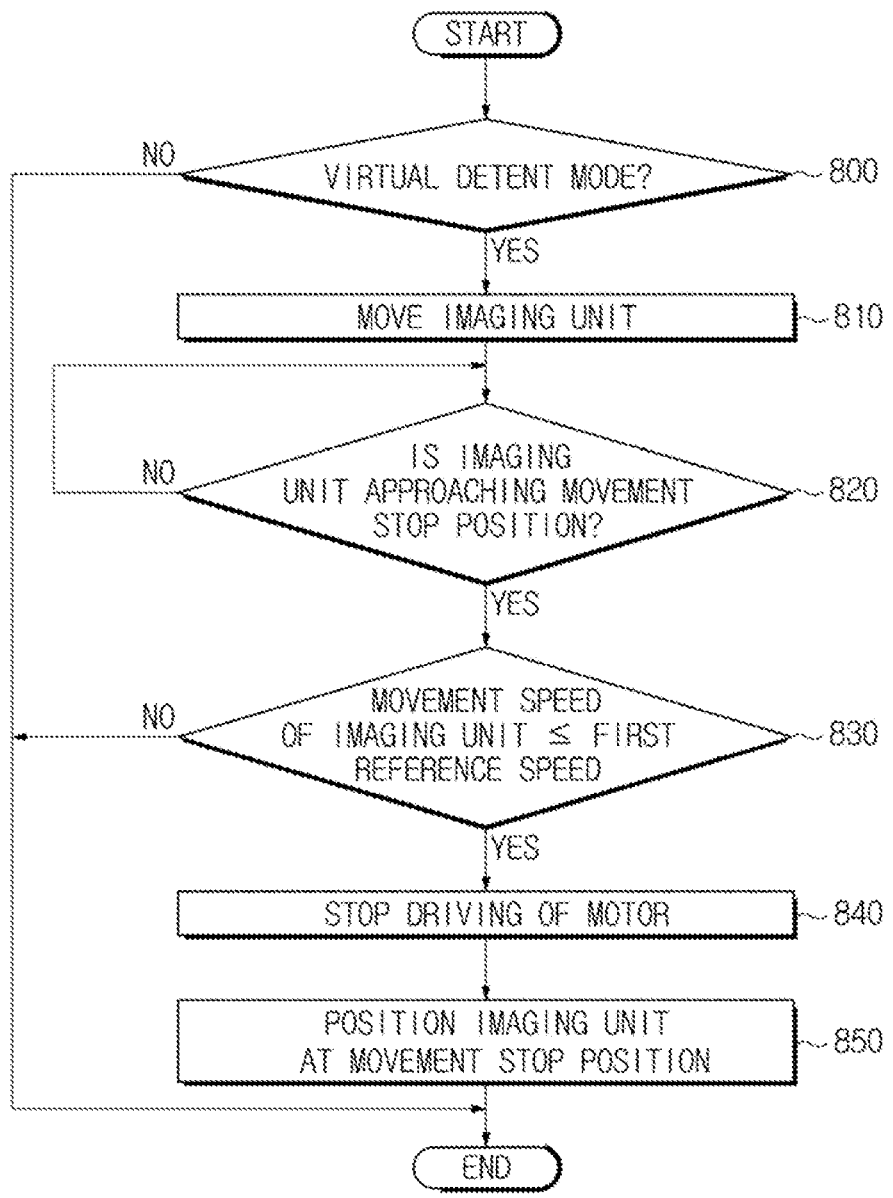
FIG. 15 is a flowchart illustrating a virtual detent mode of a radiographic imaging apparatus, according to an exemplary embodiment.

FIG. 15 is a flowchart illustrating a virtual detent mode of a radiographic imaging apparatus, according to an exemplary embodiment.

As illustrated in FIG. 15, in operation 800, the controller 41 determines whether the process is in the virtual detent mode.

An input device, such as, for example, a button that is provided in the operating panel 80 or the workstation and may turn the virtual detent mode on or off as necessary, is operated and it is determined whether the virtual detent mode is turned on.

When the virtual detent mode is in an on state and the radiographic imaging unit 70 moves in operation 810, the controller 41 determines whether the radiographic imaging unit 70 approaches the stop position in operation 820. When the radiographic imaging unit 70 approaches the stop position, in operation 830, the controller 41 determines whether the movement speed of the radiographic imaging unit 70 is less than or equal to the first reference speed. When the movement speed of the radiographic imaging unit 70 is less than or equal to the first reference speed or less, in operation 840, an operation of the motor 110 is stopped, and in operation 850, movement of the radiographic imaging unit 70 is stopped at the stop position.

In the virtual detent mode, the stop position at which movement of the radiographic imaging unit 70 is automatically stopped may be directly designated and set by the user, or may be preset and stored as a position at which the radiographic imaging unit 70 is frequently positioned. The encoder or the potentiometer detects the position of the radiographic imaging unit 70 in real time and transmits the result to the controller 41. The controller 41 determines whether the detected position of the radiographic imaging unit 70 transmitted in real time matches the stop position.

Further, a speed sensor configured to detect a movement speed of the radiographic imaging unit 70 detects the movement speed of the radiographic imaging unit 70 in real time and transmits the result to the controller 41. The controller 41 determines whether the detected movement speed of the radiographic imaging unit 70 transmitted in real time is less than or equal to the preset first reference speed at the stop position. When the detected position of the radiographic imaging unit 70 matches the stop position and the detected movement speed of the radiographic imaging unit 70 is less than or equal to the first reference speed, the controller 41 stops driving of the motor 110 which is configured to assist with movement of the radiographic imaging unit 70 and facilitates a cessation of movement of the radiographic imaging unit 70 at the stop position.

Further, the controller 41 may determine whether a real time position of the radiographic imaging unit 70 transmitted from the encoder or the potentiometer enters the stop space which has a predetermined volume that includes the stop position. In this aspect, when the position of the radiographic imaging unit 70 enters the stop space, the controller 41 determines whether the detected movement speed of the radiographic imaging unit 70 transmitted in real time is less than or equal to the first reference speed. When the detected movement speed of the radiographic imaging unit 70 is less than or equal to the first reference speed, the controller 41 decreases the movement speed of the radiographic imaging unit 70 such that the radiographic imaging unit 70 may stop at the stop position. When the stop space is set, the radiographic imaging unit 70 is not immediately stopped, but the radiographic imaging unit 70 may be stopped while the movement speed of the radiographic imaging unit 70 is decreased. Therefore, the radiographic imaging unit 70 may be stopped at the stop position more smoothly.

In the virtual detent mode, without using the brake to stop movement of the radiographic imaging unit 70, driving of the motor 110 is stopped to stop movement of the radiographic imaging unit 70. Therefore, it is possible to prevent noise or oscillation of the device that is generated when the brake is used. Further, the brake itself may be omitted.

Figure 16:
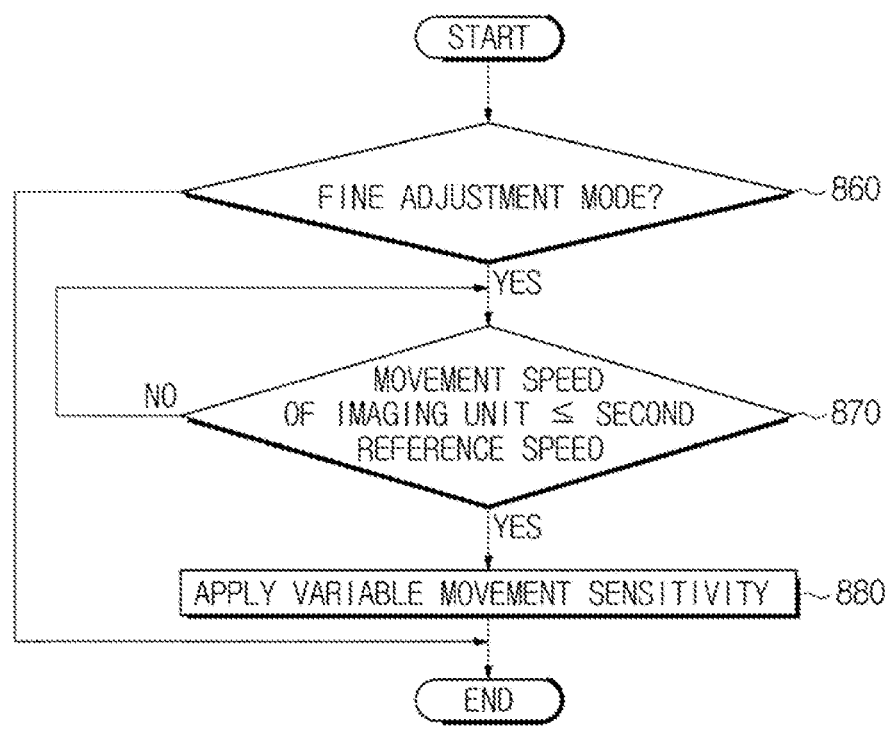
FIG. 16 is a flowchart illustrating a fine adjustment mode of a radiographic imaging apparatus, according to an exemplary embodiment.

FIG. 16 is a flowchart illustrating a fine adjustment mode of a radiographic imaging apparatus, according to an exemplary embodiment.

As illustrated in FIG. 16, in operation 860, the controller 41 determines whether the process is in the fine adjustment mode.

An input device, such as, for example, a button that is provided in the operating panel 80 or the workstation and capable of turning settings of the variable movement sensitivity on or off as necessary, is operated to determine whether the fine adjustment mode in which the variable movement sensitivity is set is turned on.

When the fine adjustment mode is in an on state, in operation 870, the controller 41 determines whether the movement speed of the radiographic imaging unit 70 is less than or equal to the second reference speed, and when the movement speed is less than or equal to the second reference speed, the variable movement sensitivity is applied in operation 880.

As illustrated in FIG. 13, when the movement speed of the radiographic imaging unit 70 is greater than the preset the second reference speed, the movement sensitivity of the radiographic imaging unit 70 is fixed as a constant value, and settings favorable for movement of the radiographic imaging unit 70 are provided. When the movement speed of the radiographic imaging unit 70 is less than or equal to the preset second reference speed, the movement sensitivity is set to be decreased as the speed of the radiographic imaging unit 70 decreases, and settings favorable for fine adjustment of the radiographic imaging unit 70 are provided.

When the movement speed of the radiographic imaging unit 70 is less than or equal to the second reference speed, the movement sensitivity of the radiographic imaging unit 70 decreases as the movement speed of the radiographic imaging unit 70 decreases. Therefore, the user may precisely control the radiographic imaging unit 70. For example, in fine adjustment, a movement sensitivity (a) when the radiographic imaging unit 70 needs to be moved at a low speed is smaller than a movement sensitivity (b) when the radiographic imaging unit 70 needs to be moved at a slightly higher speed. Accordingly, even when the movement sensitivity value of the radiographic imaging unit 70 is small, the user may adjust the position of the radiographic imaging unit 70 more accurately than when the value is fixed.

While the variable movement sensitivity is set, the speed sensor detects the movement speed of the radiographic imaging unit 70 in real time and transmits the result to the controller 41. The controller 41 adjusts the movement sensitivity according to a change in the speed of the radiographic imaging unit 70 as shown in FIG. 13 when the detected movement speed of the radiographic imaging unit 70 transmitted in real time is less than or equal to the second reference speed.

Although a few exemplary embodiments have been shown and described, it will be appreciated by those of skill in the art that changes may be made in these exemplary embodiments without departing from the principles and spirit of the present inventive concept, the scope of which is defined in the claims and their equivalents.

What is claimed is:

1. A radiographic imaging apparatus, comprising:
a radiographic image generator;
a motor configured to move the radiographic image generator and to output, as a feedback signal, information which relates to at least one from among a driving speed and a position of the motor;
a guide rail to which the motor is connected via a post frame, the guide rail being fixably attached to a ceiling, and the radiographic image generator being coupled to the post frame by a rotary joint that is configured to enable the radiographic image generator to rotate in each of a first direction about a first axis that is orthogonal to the ceiling and a second direction about a second axis that is orthogonal to the first axis and parallel to the ceiling; and a controller configured to calculate a disturbance applied to the radiographic image generator by using the feedback signal output from the motor and a control signal for driving the motor, and to drive the motor based on the calculated disturbance, wherein the controller is further configured to calculate the disturbance by subtracting the control signal for driving the motor from the feedback signal output from the motor.

2. The radiographic imaging apparatus according to claim 1, wherein the controller is further configured to calculate an external force applied to the radiographic image generator from the disturbance.

3. The radiographic imaging apparatus according to claim 2, wherein the controller is further configured to drive the motor based on an amount and a direction of the external force.

4. The radiographic imaging apparatus according to claim 2, wherein the motor is further configured to move the radiographic image generator in a direction of the external force by using a driving force which corresponds to an amount of the external force.

5. The radiographic imaging apparatus according to claim 2, wherein the controller is further configured to control at least one from among the position, the driving speed, a current, an acceleration, and an angular velocity of the motor based on an amount and a direction of the external force.

6. The radiographic imaging apparatus according to claim 2, wherein the controller is further configured to generate an input signal for controlling at least one from among the position, the driving speed, a current, an acceleration, and an angular velocity of the motor based on the external force.

7. The radiographic imaging apparatus according to claim 6, wherein the controller is further configured to receive an error signal calculated from the generated input signal and the feedback signal output from the motor, to generate the control signal for controlling at least one from among the position, the driving speed, the current, the acceleration, and the angular velocity of the motor by using at least one from among a proportional control, an integral control, and a differential control, and to transmit the generated control signal to the motor.

8. The radiographic imaging apparatus according to claim 6, wherein the controller is further configured to remove a signal of a resonance frequency band of the radiographic imaging apparatus from the generated input signal and to transmit a result of the removal to the motor.

9. The radiographic imaging apparatus according to claim 7, wherein a gain of the at least one from among the proportional control, the integral control, and the differential control is preset to have a value which is smaller than a predetermined threshold value.

10. A method for controlling a radiographic imaging apparatus, comprising:

calculating a disturbance applied to a radiographic image generator;

receiving, as feedback signal output from a motor which is configured to move the radiographic image generator, information which relates to at least one from among a driving speed and a position of the motor;

calculating an external force applied to the radiographic image generator from the disturbance by using the feedback signal output from the motor and a control signal for driving the motor; and moving the radiographic image generator based on the external force, wherein the motor is connected to a guide rail via a post frame, the guide rail is fixably attached to a ceiling, and the radiographic image generator is coupled to the post frame by a rotary joint that is configured to enable the radiographic image generator to rotate in each of a first direction about a first axis that is orthogonal to the ceiling and a second direction about a second axis that is orthogonal to the first axis and parallel to the ceiling, wherein the calculating the disturbance includes calculating the disturbance by subtracting the control signal for driving the motor from the feedback signal output from the motor which is configured to move the radiographic image generator.

11. The method according to claim 10, wherein the moving the radiographic image generator includes controlling at least one from among the position, the driving speed, a current, an acceleration, and an angular velocity of the motor which is configured to move the radiographic image generator based on an amount and a direction of the external force.

12. The method according to claim 10, wherein the moving the radiographic image generator includes:

generating an input signal for controlling at least one from among the position, the driving speed, a current, an acceleration, and an angular velocity of the motor configured to move the radiographic image generator based on an amount and a direction of the external force;

calculating an error signal by subtracting the feedback signal output from the motor from the generated input signal; and controlling at least one from among the position, the driving speed, the current, the acceleration, and the angular velocity of the motor based on the calculated error signal by using at least one from among a proportional control, an integral control, and a differential control.

13. The method according to claim 12, further comprising removing a signal of a resonance frequency band of the radiographic imaging apparatus from the generated input signal.

14. The method according to claim 12, wherein a gain of the at least one from among the proportional control, the integral control, and the differential control is preset to have a value which is smaller than a predetermined threshold value.

15. A radiographic imaging apparatus, comprising:

a radiographic image generator;

a motor configured to move the radiographic image generator and to output information which relates to at least one from among a driving speed and a position of the motor as a feedback signal;

a guide rail to which the motor is connected via a post frame, the guide rail being fixably attached to a ceiling, and the radiographic image generator being coupled to the post frame by a rotary joint that is configured to enable the radiographic image generator to rotate in each of a first direction about a first axis that is orthogonal to the ceiling and a second direction about a second axis that is orthogonal to the first axis and parallel to the ceiling; and a controller configured to provide a power-assisted mode and an automatic movement mode, and in the power-assisted mode, to calculate a disturbance applied to the radiographic image generator by using the feedback signal output from the motor and a control signal for driving the motor and drive the motor based on the calculated disturbance, and in the automatic movement mode, to move the radiographic image generator to a movement position of the radiographic image generator if the movement position of the radiographic image generator is input by a user, wherein the controller is further configured to calculate the disturbance by subtracting the control signal for driving the motor from the feedback signal output from the motor.

16. The radiographic imaging apparatus according to claim 15, further comprising a mode switching unit configured to switch the power-assisted mode and the automatic movement mode between each other in response to an input provided by the user.

17. The radiographic imaging apparatus according to claim 1, wherein the information which relates to at least one from among the driving speed and the position of the motor comprises at least one from among the driving speed of the motor with respect to the guide rail and the position of the motor with respect to the guide rail.

18. The method according to claim 10, wherein the information which relates to at least one from among the driving speed and the position of the motor comprises at least one from among the driving speed of the motor with respect to the guide rail and the position of the motor with respect to the guide rail.

19. The radiographic imaging apparatus according to claim 15, wherein the information which relates to at least one from among the driving speed and the position of the motor comprises at least one from among the driving speed of the motor with respect to the guide rail and the position of the motor with respect to the guide rail.

20. The radiographic imaging apparatus according to claim 1, wherein the disturbance comprises an external force applied to the radiographic image generator by a user and a disturbance component that is not applied by the user.

21. The radiographic imaging apparatus according to claim 20, wherein the disturbance component that is not applied by the user comprises an oscillation caused by a resonance that is generated when the external force is applied to move the radiographic image generator in a direction that is parallel to the ceiling.

22. The method according to claim 10, wherein the disturbance comprises the external force applied to the radiographic image generator by a user and a disturbance component that is not applied by the user.

23. The method according to claim 22, wherein the disturbance component that is not applied by the user comprises an oscillation caused by a resonance that is generated when the moving the radiographic image generator based on the external force occurs in a direction that is parallel to the ceiling.

* * * * *